US012622852B2

(12) United States Patent
Shah et al.

(10) Patent No.: US 12,622,852 B2
(45) Date of Patent: May 12, 2026

(54) COMPOSITIONS AND METHODS FOR STYLING HAIR

(71) Applicant: L'OREAL, Paris (FR)

(72) Inventors: Vibha K. Shah, Branchburg, NJ (US); Allison Perner, Metuchen, NJ (US); Minli Shi, Jersey City, NJ (US); Lisa Ye-Tse, Brooklyn, NY (US); Lynne Mccullough, Brooklyn, NY (US)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 17/855,765

(22) Filed: Jun. 30, 2022

(65) Prior Publication Data

US 2024/0000678 A1 Jan. 4, 2024

(51) Int. Cl.

| | |
|---|---|
| ***A61K 8/34*** | (2006.01) |
| ***A61K 8/06*** | (2006.01) |
| ***A61K 8/37*** | (2006.01) |
| ***A61K 8/73*** | (2006.01) |
| ***A61K 8/81*** | (2006.01) |
| ***A61K 8/92*** | (2006.01) |
| ***A61Q 5/06*** | (2006.01) |

(52) U.S. Cl.
CPC .............. *A61K 8/347* (2013.01); *A61K 8/062* (2013.01); *A61K 8/37* (2013.01); *A61K 8/73* (2013.01); *A61K 8/8158* (2013.01); *A61K 8/922* (2013.01); *A61Q 5/06* (2013.01)

(58) Field of Classification Search
CPC .......... A61Q 5/06; A61K 8/922; A61K 8/602; A61K 8/37; A61K 8/347; A61K 8/73; A61K 8/8152; A61K 8/062; A61K 8/8158; A61K 2800/30
See application file for complete search history.

(56) References Cited

U.S. PATENT DOCUMENTS

| | | | |
|---|---|---|---|
| 2,047,398 | A | 7/1936 | Voss et al. |
| 2,102,113 | A | 12/1937 | Djordjevitch |
| 2,723,248 | A | 11/1955 | Wright |
| 3,579,629 | A | 5/1971 | Pasero et al. |
| 3,589,978 | A | 6/1971 | Kamal et al. |
| 3,734,874 | A | 5/1973 | Kibler et al. |
| 3,779,993 | A | 12/1973 | Kibler et al. |
| 3,810,977 | A | 5/1974 | Levine et al. |
| 3,836,537 | A | 9/1974 | Boerwinkle et al. |

(Continued)

FOREIGN PATENT DOCUMENTS

| | | | |
|---|---|---|---|
| CN | 1422143 | A | 6/2003 |
| CN | 1452477 | A | 10/2003 |

(Continued)

OTHER PUBLICATIONS

Non-Final Office Action for copending U.S. Appl. No. 17/131,335, dated Sep. 1, 2023.

(Continued)

*Primary Examiner* — Hong Yu
(74) *Attorney, Agent, or Firm* — The Marbury Law Group, PLLC

(57) ABSTRACT

The disclosure relates to hair styling compositions comprising (a) at least one polyphenol; (b) at least one polysaccharide gum; (c) at least one polymeric emulsifier; (d) glyceryl polyacrylate; and (e) water. The disclosure also relates to methods of using the compositions, for example to straighten hair.

20 Claims, 7 Drawing Sheets

(56) References Cited

U.S. PATENT DOCUMENTS

| | | | |
|---|---|---|---|
| 3,910,862 A | 10/1975 | Barabas et al. | |
| 3,946,749 A | 3/1976 | Papantoniou | |
| 3,966,403 A | 6/1976 | Papantoniou et al. | |
| 3,966,404 A | 6/1976 | Papantoniou et al. | |
| 4,031,307 A | 6/1977 | DeMartino et al. | |
| 4,119,680 A | 10/1978 | Vachon | |
| 4,128,631 A | 12/1978 | Lundmark et al. | |
| 4,131,576 A | 12/1978 | Iovine et al. | |
| 4,137,180 A | 1/1979 | Naik et al. | |
| 4,137,208 A | 1/1979 | Elliott | |
| 4,165,367 A | 8/1979 | Chakrabarti | |
| 4,282,203 A | 8/1981 | Jacquet et al. | |
| 4,289,752 A | 9/1981 | Mahieu et al. | |
| 4,300,580 A | 11/1981 | O'Neill et al. | |
| 4,517,175 A | 5/1985 | Iwabuchi et al. | |
| 4,693,935 A | 9/1987 | Mazurek | |
| 4,728,571 A | 3/1988 | Clemens et al. | |
| 4,874,554 A | 10/1989 | Lange et al. | |
| 4,972,037 A | 11/1990 | Garbe et al. | |
| 4,973,656 A | 11/1990 | Blount | |
| 5,198,217 A | 3/1993 | Vedros | |
| 5,277,899 A | 1/1994 | McCall | |
| 5,538,717 A | 7/1996 | La Poterie | |
| 5,660,816 A | 8/1997 | Adams et al. | |
| 5,660,818 A | 8/1997 | Dubief et al. | |
| 5,662,893 A | 9/1997 | George et al. | |
| 5,674,479 A | 10/1997 | George et al. | |
| 5,686,082 A | 11/1997 | N'Guyen | |
| 5,792,448 A | 8/1998 | Dubief et al. | |
| 6,106,813 A | 8/2000 | Mondet et al. | |
| 6,166,093 A | 12/2000 | Mougin et al. | |
| 6,214,329 B1 | 4/2001 | Brieva et al. | |
| 6,395,265 B1 | 5/2002 | Mougin et al. | |
| 6,482,942 B1 | 11/2002 | Vittori | |
| 7,151,079 B2 | 12/2006 | Fack et al. | |
| 8,551,503 B2 | 10/2013 | Segura-Orsoni et al. | |
| 10,052,273 B2 | 8/2018 | Lalleman et al. | |
| 10,327,999 B2 | 6/2019 | Knappe et al. | |
| 11,311,473 B2 | 4/2022 | Fischer et al. | |
| 2002/0034486 A1 | 3/2002 | Midha et al. | |
| 2003/0064038 A1 | 4/2003 | Auguste et al. | |
| 2003/0175230 A1 | 9/2003 | Dubief | |
| 2004/0132699 A1 | 7/2004 | Zhuang et al. | |
| 2006/0134049 A1 | 6/2006 | Keenan et al. | |
| 2007/0264220 A1* | 11/2007 | Hiraishi | A61K 8/92 424/70.31 |
| 2008/0031841 A1 | 2/2008 | Laurent et al. | |
| 2008/0112897 A1* | 5/2008 | Schiemann | A61Q 5/12 424/47 |
| 2009/0042846 A1 | 2/2009 | Gupta | |
| 2012/0230925 A1* | 9/2012 | Wagner | C11C 5/002 510/214 |
| 2013/0109746 A1 | 5/2013 | Derkx et al. | |
| 2013/0202546 A1 | 8/2013 | Howell | |
| 2013/0232701 A1 | 9/2013 | Aimi et al. | |
| 2014/0093466 A1 | 4/2014 | Combs et al. | |
| 2016/0007708 A1* | 1/2016 | Castro | A46B 15/003 132/269 |
| 2017/0340542 A1 | 11/2017 | Lalleman et al. | |
| 2017/0354584 A1 | 12/2017 | Lalleman et al. | |
| 2018/0104161 A1 | 4/2018 | Siddiqui | |
| 2018/0344619 A1 | 12/2018 | Sun et al. | |
| 2018/0346653 A1 | 12/2018 | Dussaud et al. | |
| 2018/0353401 A1 | 12/2018 | Wossene et al. | |
| 2019/0159995 A1 | 5/2019 | Ebanks et al. | |
| 2019/0224093 A1 | 7/2019 | Furukawa et al. | |
| 2019/0314252 A1 | 10/2019 | Iwatani et al. | |
| 2020/0129407 A1 | 4/2020 | Noll et al. | |
| 2021/0196594 A1 | 7/2021 | Khine et al. | |
| 2021/0196609 A1 | 7/2021 | Parekh et al. | |

FOREIGN PATENT DOCUMENTS

| | | | |
|---|---|---|---|
| CN | 104257544 | A | 1/2015 |
| CN | 106511104 | A | 3/2017 |
| CN | 106821840 | A | 6/2017 |
| CN | 109562033 | A | 4/2019 |
| CN | 110123668 | A | 8/2019 |
| CN | 110300573 | A | 10/2019 |
| CN | 110820336 | A | 2/2020 |
| DE | 2330956 | A1 | 1/1974 |
| EP | 0412704 | A2 | 2/1991 |
| EP | 0412707 | A1 | 2/1991 |
| EP | 0507272 | A1 | 10/1992 |
| EP | 0582152 | A2 | 2/1994 |
| EP | 0619111 | A1 | 10/1994 |
| EP | 0637600 | A1 | 2/1995 |
| EP | 0640105 | A1 | 3/1995 |
| EP | 0648485 | A1 | 4/1995 |
| EP | 0656021 | A1 | 6/1995 |
| EP | 0680744 | A1 | 11/1995 |
| EP | 0751162 | A1 | 1/1997 |
| EP | 1927378 | A1 | 6/2008 |
| EP | 2938321 | A2 | 11/2015 |
| EP | 3403642 | A1 | 11/2018 |
| FR | 1222944 | A | 6/1960 |
| FR | 1564110 | A | 4/1969 |
| FR | 1580545 | A | 9/1969 |
| FR | 2077143 | A5 | 10/1971 |
| FR | 2198719 | A1 | 4/1974 |
| FR | 2265781 | A1 | 10/1975 |
| FR | 2265782 | A1 | 10/1975 |
| FR | 2350384 | A1 | 12/1977 |
| FR | 2357241 | A2 | 2/1978 |
| FR | 2393573 | A1 | 1/1979 |
| FR | 2439798 | A1 | 5/1980 |
| FR | 2743297 | A1 | 7/1997 |
| FR | 2892625 | A1 | 5/2007 |
| FR | 2956809 | A1 | 9/2011 |
| FR | 2981569 | A1 | 4/2013 |
| FR | 3059900 | A1 | 6/2018 |
| GB | 839805 | A | 6/1960 |
| GB | 922457 | A | 4/1963 |
| GB | 1408388 | A | 10/1975 |
| GB | 1572626 | A | 7/1980 |
| JP | 3966825 | B2 | 8/2007 |
| JP | 2008-247761 | A | 10/2008 |
| JP | 2012-214453 | A | 11/2012 |
| JP | 2013-053086 | A | 3/2013 |
| JP | 2019-202968 | A | 11/2019 |
| KR | 10-2010-0026712 | A | 3/2010 |
| LU | 75370 | A1 | 2/1978 |
| LU | 75371 | A1 | 2/1978 |
| TW | 201400133 | A | 1/2014 |
| WO | 93/23009 | A1 | 11/1993 |
| WO | 93/23446 | A2 | 11/1993 |
| WO | 94/03510 | A1 | 2/1994 |
| WO | 95/00578 | A1 | 1/1995 |
| WO | 95/18191 | A1 | 7/1995 |
| WO | 97/08261 | A1 | 3/1997 |
| WO | 97/20899 | A1 | 6/1997 |
| WO | 0191705 | A1 | 12/2001 |
| WO | 2013131756 | A2 | 9/2013 |
| WO | 2014/102251 | A2 | 7/2014 |
| WO | 2014145057 | A1 | 9/2014 |
| WO | 2017195841 | A1 | 11/2017 |
| WO | 2019/197852 | A1 | 10/2019 |
| WO | 2019/200027 | A1 | 10/2019 |
| WO | 2019195900 | A1 | 10/2019 |
| WO | 2019195901 | A1 | 10/2019 |
| WO | 2019212710 | A1 | 11/2019 |
| WO | 2021/133867 | A1 | 7/2021 |

OTHER PUBLICATIONS

Non-Final Office Action for copending U.S. Appl. No. 17/853,071, dated Sep. 14, 2023.-

(56) References Cited

OTHER PUBLICATIONS

Chinese Office Action and Search Report for counterpart Application No. 202080089561.7, dated Jul. 20, 2023 (translation unavailable).
French Search Report for counterpart Application No. FR2209186, issued May 9, 2023.
French Search Report and Written Opinion for counterpart Application No. FR2211644, dated Jun. 6, 2023.
Mintel: "Anti-Frizz Cream," Anaber Cometicos Ind. E. Com, Record ID 778779, XP093050505, dated Oct. 26, 2007.
Mintel: "Breakage Strengthening Scalp Serum for Weak Hair," Niche Beauty Lab, Record ID 9764688, XP093050554, Aug. 9, 2022.
Mintel: "No. 6 Bond Smoother," Olaplex, Record ID 9746722, XP093050562, Jul. 14, 2022.
Final Office Action for copending U.S. Appl. No. 17/130,273, dated Aug. 2, 2023.
Final Office Action for copending U.S. Appl. No. 17/131,335, dated Feb. 24, 2023.
Co-pending U.S. Appl. No. 17/130,273, entitled "Compositions and Methods for Styling Hair," Inventors: Aakash Jagat Parekh et al., filed Dec. 22, 2020.
Co-pending U.S. Appl. No. 17/131,335, entitled "Compositions and Methods for Eyelashes," Inventors: Cho-Cho Khine et al., filed Dec. 22, 2020.
Lechocinski, N., et al., "Fiber orientation measurement using polarization imaging," J. Cosmet. Sci., 62, (Mar./Apr. 2011), pp. 85-100.
Mintel: "Wax," Angfa, XP055795379, Database Accession No. 4548051, Jan. 12, 2017.
Mintel: "Black Eyelash Tint," Tana Cosmetics, XP055792645, Record ID 540089, Jun. 5, 2006, pp. 1-2.
International Search Report and Written Opinion for counterpart Application No. PCT/US2020/066763, dated Apr. 23, 2021.
International Search Report and Written Opinion for counterpart Application No. PCT/US2020/066939, dated Apr. 19, 2021.
Mintel: "Vivid Volume & Length Double Effect Mascara," Wei Ke Le Cosmetics, XP055792650, Database accession No. 5788913, Jun. 28, 2018.
Mintel: "Magical Fast-Drying Mascara," Magic Mirror Group, XP055792678, Database accession No. 5601775, Apr. 17, 2018.
Co-pending U.S. Appl. No. 17/853,580, entitled "Compositions and Methods for Styling Hair," Inventors: Rachel Ferebee Maher et al., filed Jun. 29, 2022.
Co-pending U.S. Appl. No. 17/852,729, entitled "Compositions and Methods for Styling Hair," Inventors: Vibha K. Shah, filed Jun. 29, 2022.
Co-pending U.S. Appl. No. 17/853,128, entitled "Compositions and Methods for Styling Hair," Inventors: Vibha K. Shah, filed Jun. 29, 2022.
Co-pending U.S. Appl. No. 17/853,071, entitled "Compositions and Methods for Styling Hair," Inventors: Vibha K. Shah et al., filed Jun. 29, 2022.
French Search Report and Written Opinion for counterpart French Application No. 2109872, dated Jun. 9, 2022.
Mintel: "Gold Fulvic Conditioner," Deciem, Record No. 4406127, XP055928358, Jan. 31, 2017.
French Search Report and Written Opinion for counterpart French Application No. 2109862, dated Jun. 9, 2022.
Mintel: "Sleek Flow Cherry & Lilac Styling Cream," I-ne, Record ID 8707019, XP055928346, May 13, 2021.
Mintel: "Smoothing Hair Treatment," Grown Alchemist, Record No. 6419291, XP055928395, Mar. 21, 2019.
French Search Report and Written Opinion for counterpart Application No. 2109867, dated Jun. 10, 2022.
Mintel: "Keratin Sealer, " Davines, Record ID 7938505, XP055929517, Jul. 7, 2020.
French Search Report and Written Opinion for counterpart Application No. 2109871, dated Jun. 9, 2022.
Mintel: "Vegetarian Miracle Conditioner," Davines, Record ID 7910153, XP055929519, Jun. 30, 2020.
International Preliminary Report on Patentability for counterpart Application No. PCT/US2020/066763, dated Jul. 7, 2022.
International Preliminary Report on Patentability for counterpart Application No. PCT/US2020/066939, dated Jul. 7, 2022.
Non-Final Office Action for copending U.S. Appl. No. 17/131,335, dated Sep. 20, 2022.
Non-Final Office Action for copending U.S. Appl. No. 17/130,273, dated Dec. 6, 2022.
International Search Report and Written Opinion for counterpart Application No. PCT/US2022/035722, dated Oct. 11, 2022.
Mintel: "Blowout Bombe," Cuvée Beauty, Record ID 6184235, XP055966277, Dated Dec. 17, 2018.
Mintel: "Spun Satin Feather Light Styling Soufflé," TIGI, Record ID 1210769, XP055966282, dated Nov. 11, 2009.
Mintel: "Texture Defining Lotion," Back to Basics Products, Record ID 690828, XP055966286, dated Apr. 13, 2007.
International Search Report and Written Opinion for counterpart Application No. PCT/US2022/035721, dated Oct. 13, 2022.
Mintel: "Cys-Treatment Straightening Hair Treatment," StylingLife Holdings, Record ID 1592789, XP055576886, dated Jun. 30, 2011.
Mintel: "BTX Hair Mask," Cedral Indústria de Cosméticos, Record No. 7121607, XP055755362, dated Dec. 20, 2019.
Mintel: "Lisoplastia Intense Straightening and Realigning of Hair Fiber," I Like Cosméticos, Record ID 8415629, XP055968116, dated Jan. 19, 2021.
Mintel: "Straight Hair Treatment," Mediplus, Record No. 6309843, XP055968002, dated Jan. 31, 2019.
Mintel: "Volume Control Mask," Garden Indústria e Comércio de Cosméticos; Record No. 4505773, XP055968006, dated Jan. 3, 2017.
Mintel: "Anti-Frizz Balm," Fekkai Brands; Record ID 5861079, XP055968148, dated Aug. 20, 2018.
International Preliminary Report on Patentability in PCT/US2022/035722, mailed Dec. 14, 2023, 12 pages.
International Preliminary Report on Patentability in PCT/US2022/035721, mailed Dec. 14, 2023, 11 pages.
Translation of Office Action in CN202080090614.7, mailed Feb. 27, 2024, 17 pages.
Office Action in CN202080089561.7, mailed Mar. 30, 2024, 12 pages.
Office Action in U.S. Appl. No. 17/853,071, mailed Nov. 14, 2024, 23 pages.
Office Action in U.S. Appl. No. 17/131,335, mailed Dec. 17, 2024, 16 pages.
Office Action in U.S. Appl. No. 17/853,128, mailed Dec. 17, 2024, 13 pages.
Translation of Second Chinese Office Action for counterpart Application No. 202080090614.7, dated Dec. 25, 2024.
Non-Final Office Action for copending U.S. Appl. No. 17/852,729, dated Jan. 6, 2025.
Draelos, "Essentials of Hair Care often Neglected: Hair Cleansing," International Journal of Trichology, Jan.-Jun. 2010, vol. 2, Issue 1, pp. 24-29.
Office Action in U.S. Appl. No. 17/853,580, mailed Feb. 26, 2025, 20 pages.
Office Action in U.S. Appl. No. 17/852,729, mailed Dec. 17, 2025, 15 pages.
Office Action in U.S. Appl. No. 17/853,128, mailed Aug. 20, 2025, 19 pages.
Office Action in U.S. Appl. No. 17/853,580, mailed Jul. 17, 2025, 26 pages.
Office Action in U.S. Appl. No. 17/853,071, mailed Jun. 25, 2025, 32 pages.
Deffaugt-Sanchez, Coline. "Hair Care Advice at the Pharmacy: From Cosmetic Advice to Drug Treatments." Pharmaceutical Sciences (2011): 1-166.
Huanbutta et al. "Use of seed gums from Tamarindus indica and Cassia fistula as controlled-release agents." Asian journal of pharmaceutical sciences 13.5 (2018): 398-408.
Office Action in EP20841837.6, mailed Apr. 7, 2025, 8 pages.
Rao et al. "Effect of β-cyclodextrin on Rheological Properties of some Viscosity Modifiers." Indian Journal of Pharmaceutical Sciences 76.6 (2014): 545-548.

(56) References Cited

OTHER PUBLICATIONS

Yang, J. "Hair Care Cosmetics," Cosmetic science and technology: theoretical principles and applications. Elsevier (2017): 601-615.
Office Action in U.S. Appl. No. 17/853,128, mailed Jan. 28, 2026, 18 pages.
Office Action in U.S. Appl. No. 17/853,071, mailed Apr. 3, 2026, 24 pages.
USPTO artificial intelligence top results, printed 2026, 1 page.

* cited by examiner

COMPOSITIONS AND METHODS FOR STYLING HAIR

TECHNICAL FIELD

The present disclosure relates to compositions and methods for styling hair, particularly, to compositions and methods for temporarily straightening curly or wavy hair.

BACKGROUND

Consumers with curly or wavy hair often desire to temporarily straighten their hair for a change in appearance, and then switch back to their curly style without damage. In addition, reducing the curls of very curly hair may increase the manageability and ease of styling of such hair.

Currently, temporary straightening curly/wavy hair or frizzy hair typically involves the use of hot tools such as blow dryers and/or flat irons. The high temperature of the blow dryers and/or irons leads to a breakage of hydrogen bonds in the keratin of the hair, achieving a temporary straightening. The hydrogen bonds are formed again by the action of moisture, so that the hair reverts back to its original shape over the time because of air humidity or after washing or damping the hair.

Longer-term and/or permanent straightening is usually achieved by using chemical straightening treatments, such as relaxers, with high pH. The shape of the hair is largely determined by the disulfide bonds linking two cysteine moieties of the hair keratin. To achieve a longer-term and/or permanent shaping or styling effect, it usually involves cleavage of the disulfide bonds by the action of a sulfide- or thiol-group containing reducing agent or relaxing agent. After the hair has been brought into the desired shape, new disulfide bonds are formed by applying an oxidizing agent such as hydrogen peroxide, thus fixing the shape of the hair. The use of such agents, however, may cause damage to the hair and weaken the hair, resulting in subsequent breakage. Conventional products that provide hold, such as styling gels, although may also provide straightening effects to the hair, usually flake on the hair and result in very stiff and unnatural look hair. In addition, conventional hair straightening routines are usually time-consuming.

As such, there is a need for new and improved compositions that can be simply applied to hair and provide straightening effects to curly or wavy hair that would not damage the hair, while imparting various additional sensorial properties to the hair such as frizz control, softness, smoothness, and/or shine. The present disclosure addresses these needs and concerns and relates to new compositions and methods that can provide styling effect, particularly, a temporary straightening effect on curly/waving hair without the requirement of using heat.

It has now surprisingly been found that a combination of components described herein allows for a balance between straightening performance and consumer desired look and feel, even under high humidity condition, and is useful for providing desired temporarily straightening effect to curly or wavy hair through a simple application routine without the use of hot tools or harsh chemicals such as reducing agents or relaxers, while at the same time delivering additional advantageous sensorial benefits such as frizz control, natural look and feel, to the hair. The temporary straightening effect and other benefits such as frizz control imparted to the hair are lasting, such as may last under high humidity conditions and until the next hair wash, without any damage to the natural curls.

SUMMARY

The present disclosure relates to compositions that provide temporary straightening effect to curly or wavy hair, while at the same time providing one or more additional benefits such as frizz control, softness, smoothness, and/or shine to the hair. The compositions may be used as leave-in compositions for styling hair, such as for temporarily straightening the hair, and may at the same time providing frizz control and/or other sensorial benefits to the hair, without the use of heat or chemical relaxers. The disclosure also relates to methods of using the compositions for styling hair, in particular, temporarily straightening curly/wavy hair, while in some embodiments further providing additional sensorial benefits such as frizz control to the hair.

In various embodiments, the hair styling compositions according to the present disclosure comprise (a) at least one polyphenol; (b) at least one polysaccharide gum; (c) at least one polymeric emulsifier; (d) glyceryl polyacrylate; and (e) water. Optionally, the compositions may further comprise at least one latex type film former chosen from acrylate-based polymers, polyurethane-based polymers, derivatives thereof, or combinations thereof at least one vegetable oil; at least one humectant; and/or at least one ester other than glyceryl polyacrylate.

In various embodiments, the hair styling compositions disclosed herein are free or substantially free of chemical relaxing agents or reducing agents. In certain embodiments, the compositions may be free or substantially free of fatty alcohols. In some further embodiments, the composition disclosed herein may be free or substantially free of cationic polymers. In further embodiments, the compositions may be free or substantially free of dyes and colorants. The hair styling compositions may have a pH of less than 7, such as, for example, from about 4 to about 6, or from about 5 to about 6. The compositions are typically in the form of an oil-in-water emulsion.

The at least one polyphenol, in various embodiments, may be chosen from flavonoids and non-flavonoids, as well as mixtures thereof. In a particular embodiment, the at least one polyphenol is chosen from flavonoids. In one exemplary and non-limiting embodiment, at least one polyphenol is tannic acid. The at least one polyphenol may be present in an amount ranging from about 0.5% to about 8% by weight, relative to the total weight of the composition, such as, for example, from about 0.5% to about 6%, from about 0.5% to about 4%, or from about 1% to about 3% by weight, relative to the total weight of the composition. In some embodiments, the composition comprises tannic acid in an amount less than 2% by weight, relative to the total weight of the composition.

In various embodiments, the at least one polysaccharide gum is present in an amount ranging from about 0.1% to about 2% by weight, relative to the total weight of the composition. In some further embodiments, at least one polysaccharide gum is chosen from sclerotium gum, gum arabic, tragacanth gum, karaya gum, guar gum, gellan gum, tara gum, locust bean gum, tamarind gum, xanthan gum, carrageenan gum dehydroxanthan gum, seneca gum, gellan gum, or mixtures thereof.

In various embodiments, the at least one polymeric emulsifier is present in an amount ranging from about 0.1% to about 10% by weight, relative to the total weight of the composition. In some embodiments, polymeric emulsifiers included in the compositions comprise, consist essentially of, or consist of polyacrylamide.

In various embodiments, the total amount of glyceryl polyacrylate in the compositions ranges from about 0.01% to about 1% by weight, such as from about 0.05% to about 0.8%, from about 0.05% to about 0.6%, from about 0.05% to about 0.4%, from or from about 0.1% to about 0.4% by weight, relative to the total weight of the composition.

In various embodiments, polyphenol and glyceryl polyacrylate included in the compositions have a weight ratio of polyphenol(s):glyceryl polyacrylate ranging from about 3:1 to about 10:1, for example, from about 3:1 to about 8:1.

In various embodiments, water is present in an amount of at least 70% by weight, such as from about 70% to about 96%, from about 80% to about 95%, from about 85% to about 95% by weight, relative to the total weight of the composition.

If present, the at least one latex type film former chosen from acrylate-based polymers, polyurethane-based polymers, derivatives thereof, or combinations thereof may be chosen from acrylates copolymer, polyurethane, derivatives thereof, or combinations thereof. In some embodiments, the acrylate-based polymers or derivatives thereof are chosen from acrylates copolymer of two or more monomers of (meth)acrylic acid or one of their simple ester, styrene/acrylates copolymer, acrylates/ethylhexyl acrylate copolymer, or mixtures thereof. In at least certain embodiments, at least one latex type film former is acrylates copolymer. In some embodiments, if present, the total amount of the at least one latex type film former may be up to about 10% by weight, such as, for example, from about 0.5% to about 8%, from about 0.5% to about 5%, from about 0.5 to about 3% by weight, relative to the total weight of the composition.

If present, the at least one vegetable oil may, for example, be chosen from coconut oil, olive oil, castor seed oil, butyrospermum Parkii (Shea) butter, soybean oil, canola oil, rapeseed oil, corn oil, cottonseed oil, palm oil, peanut oil, safflower oil, sesame oil, sunflower oil, linseed oil, palm kernel oil, tung oil, jatropha oil, mustard oil, camelina oil, pennycress oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, walnut oil, or mixtures thereof. In certain embodiments, the compositions comprise at least one vegetable oil in an amount ranging from about from about 1% to about 20% by weight, relative to the total weight of the composition.

If present, the at least one humectant may be chosen from sorbitol, sorbitol glycerin, glycerin, propylene glycol, butylene glycol, pentylene glycol, hexylene glycol, dipropylene glycol, diethylene glycol, diglycerol, hyaluronic acid, xylitol, inulin, or mixtures thereof. In certain embodiments, the compositions comprise at least one humectant in an amount ranging from about 0.1% to about 10% by weight, such as, for example, from about 0.2% to about 8%, from about 0.2% to about 5% or about 0.2% to about 1% by weight, relative to the total weight of the composition.

If present, the at least one ester other than glyceryl polyacrylate is present in an amount ranging from about 0.1% to about 5% by weight, relative to the total weight of the composition.

In certain embodiments, a hair styling composition according to the present disclosure may comprise (a) tannic acid, present in a total amount ranging from about 0.5% to about 8% by weight; (b) at least one polysaccharide gum, present in a total amount ranging from about 0.1% to about 2% by weight; (c) at least one emulsifier comprising polyacrylamide, present in a total amount ranging from about 0.1% to about 10% by weight; (d) glyceryl polyacrylate, present in an amount ranging from about 0.05% to about 1% by weight, relative to the total weight of the composition; (e) water, present in an amount of at least 70%; where all amounts are based on the total amount of the hair styling composition. Optionally, the compositions may further comprise at least one latex type film former chosen from acrylate-based polymers, polyurethane-based polymers, derivatives thereof, or combinations thereof, present in a total amount ranging from about 0.01% to about 10% by weight; at least one vegetable oil; at least one humectant; and at least one ester other than glyceryl polyacrylate. The hair styling compositions may have a pH of less than 7, and may, for example, be formulated in the form of an oil-in-water emulsion.

In various embodiments, the present disclosure also relates to methods for temporarily straightening curly or wavy hair. The methods comprise applying to hair, for example, curly or wavy hair, any of the hair styling compositions described herein; and straightening the hair applied with the hair styling composition, for example by combing through with fingers or a comb.

The compositions used in the methods may, in various embodiments, comprise (a) at least one polyphenol; (b) at least one polysaccharide gum; (c) at least one polymeric emulsifier; (d) glyceryl polyacrylate; and (e) water, and optionally: at least one latex type film former chosen from acrylate-based polymers, polyurethane-based polymers, derivatives thereof, or combinations thereof; at least one vegetable oil; at least one humectant; and/or at least one ester other than glyceryl polyacrylate. The hair styling compositions may, for example, be in the form of an oil-in-water emulsion, and may have a pH of less than 7, such as, for example, from about 4 to about 6. The compositions may be used as leave-in compositions. In some embodiments, the hair styling composition used in the methods may be free or substantially free of fatty alcohols. In some further embodiments, the hair styling composition may be free or substantially free of cationic polymers. The methods disclosed typically do not require the use of heat or chemical relaxer before, during, or after styling the hair using the compositions disclosed herein.

BRIEF DESCRIPTION OF THE FIGURES

The accompanying figures, which are incorporated herein and constitute part of this specification, illustrate exemplary embodiments of the disclosure, and, together with the general description given above and the description provided herein, serve to demonstrate features of the disclosure.

Figure 1:
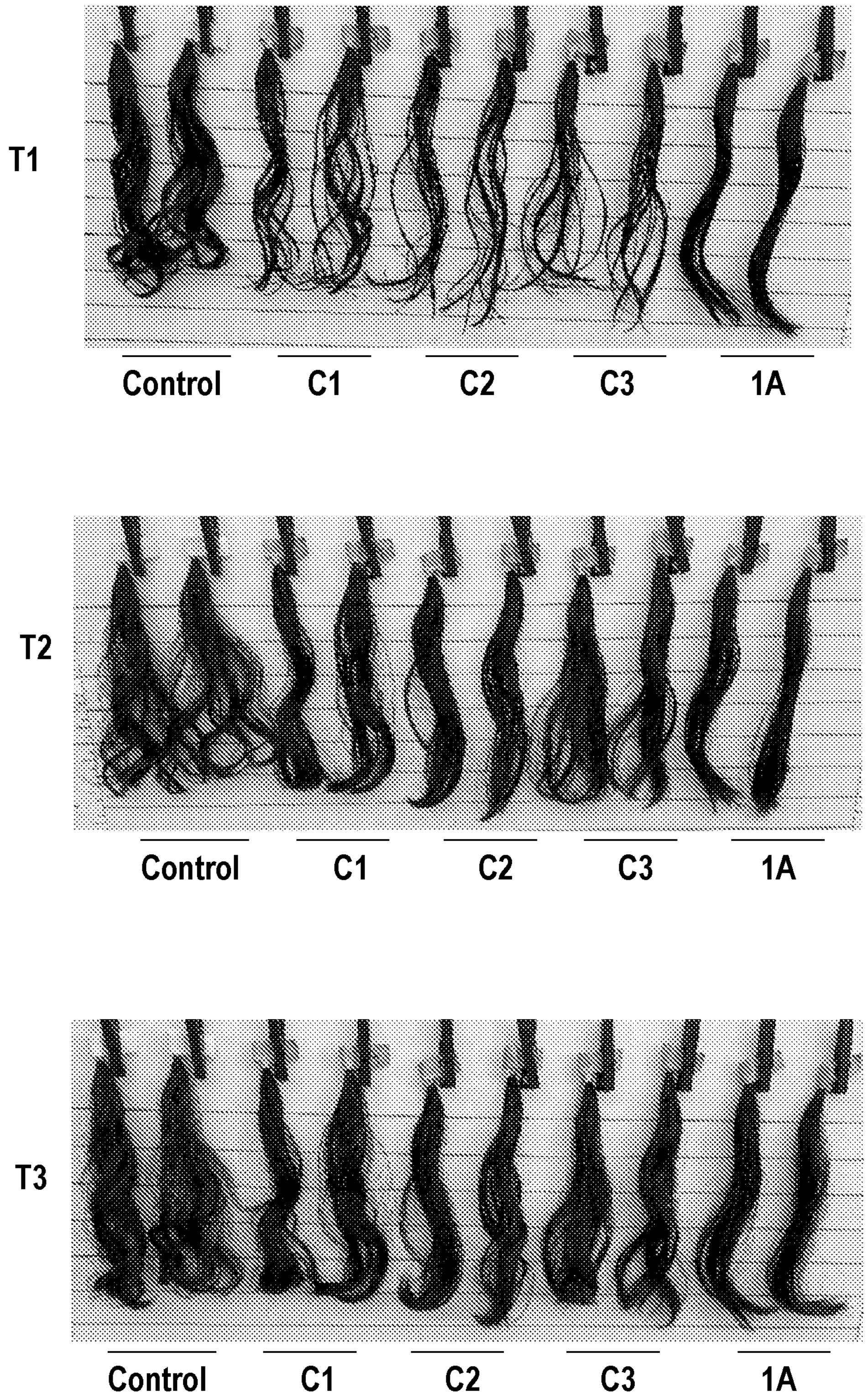
FIG. 1 is a set of photographs showing the appearance of the hair swatches treated with composition 1A according to the present disclosure and comparative compositions C1-C3, compared to a control hair swatch treated with water, while the hair was still wet (T1), after the hair was detangled and dried (T2), and after the hair was exposed to a condition of 80% relative humidity (RH) at room temperature for one hour.

It is to be understood that the foregoing and following descriptions are exemplary and explanatory only, and are not intended to be restrictive of any subject matter claimed.

DETAILED DESCRIPTION

The disclosure relates to hair styling compositions that can temporarily straighten wavy or curly hair. The compositions can further impart one or more additional sensorial benefits to the hair. The disclosure also relates to methods of using the compositions for styling hair.

I. Compositions

In various embodiments, compositions according to the disclosure comprise (a) at least one polyphenol; (b) at least one polysaccharide gum; (c) at least one polymeric emulsifier; (d) glyceryl polyacrylate; and (e) water. Optionally, the compositions may further comprise at least one latex type film former chosen from acrylate-based polymers, polyurethane-based polymers, derivatives thereof, or combinations thereof; at least one vegetable oil; at least one humectant; and/or at least one ester other than glyceryl polyacrylate. The compositions may, in some embodiments, be free or substantially free of fatty alcohols. In some further embodiments, the compositions may be free or substantially free of cationic polymers. The compositions may, in various embodiments, be in the form of an oil-in-water emulsion. The compositions typically have pH of less than 7, and can be used as leave-in compositions.

Polyphenols

Compositions according to the disclosure comprise at least one polyphenol. Polyphenols are phenols with more than one phenolic —OH group that have the ability to act as "donor molecules" by donating their alcoholic hydrogen or accepting delocalized electrons. The two classes of polyphenols are flavonoids and non-flavonoids.

Exemplary and non-limiting flavonoid compounds that can be used include, for example, tannins, such as ellagitannins, tannic acid, gallic acid, or ellagic acid; flavanols, such as catechin, fisetin, kaempferol, myricetin, quercetin, rutin, proanthocyanidins, pyroanthocyanidins, theaflavins, or thearubigins (or thearubrins); dihydroflavonols, such as astilbin, dihydroquercetin, or silibinin; flavanones, such as hesperidin, neohesperidin, hesperetin, naringenin, naringin, or poncirin; flavones, such as apigenin, baicalin, diosmin, or rhoifolin; isoflavonoids, such as biochanin A, Daidzein, or Genistein; fulvic acid, and neoflavonoids, as well as combinations thereof.

Exemplary and non-limiting non-flavonoid compounds that can be used include, for example, stibenoids such as astringin, resveratrol, or rhaponticin, as well as combinations thereof.

Other polyphenols that can be used include hydroxycinnamic acids, for example, chlorogenic acid, verbascoside; phenolic aldehydes; phenylpropenes; coumarins, coumestans, or tyrosols, as well as combinations thereof. In some embodiments, the polyphenols may be plant-based and/or organic.

In certain exemplary embodiments, polyphenols useful according to the disclosure may be chosen from tannic acid, resveratrol, catechin, ellagic acid, resorcinol, gallic acid, humic acid, chlorogenic acid, quercetin, chebulinic acid, or mixtures thereof. In certain embodiments, the polyphenols are chosen from polyphenols that do not impart color to the hair. In some embodiments, the polyphenol chosen comprises, consists essentially of, or consists of tannic acid. In some embodiments, the polyphenol comprises tannic acid and at least one other polyphenol, for example tannic acid and at least one other flavonoid compound.

In various embodiments, the total amount of polyphenol(s) present in the compositions may range from about 0.1% to about 8%, including all subranges therebetween, such as from about 0.1% to about 7%, from about 0.1% to about 6%, from about 0.1% to about 5%, from about 0.1% to about 4%, from about 0.1% to about 3%, from about 0.5% to about 8%, from about 0.5% to about 7%, from about 0.5% to about 6%, from about 0.5% to about 5%, from about 0.5% to about 4%, from about 0.5% to about 3%, from about 0.75% to about 8%, from about 0.75% to about 7%, from about 0.75% to about 6%, from about 0.75% to about 5%, from about 0.75% to about 4%, from about 0.75% to about 3%, from about 1% to about 8%, from about 1% to about 7%, from about 1% to about 6%, from about 1% to about 5%, from about 1% to about 4%, or from about 1% to about 3% by weight, relative to the total weight of the composition, including all ranges and subranges thereof. In some embodiments, the total amount of polyphenol(s) ranges from about 0.5% to about 7% or from about 1% to about 6% by weight, relative to the total weight of the composition.

In some embodiments, the compositions disclosed herein comprise tannic acid, wherein the tannic acid is present in an amount ranging from about 0.1% to about 8%, such as from about 0.1% to about 7%, from about 0.1% to about 6%, from about 0.5% to about 8%, from about 0.5% to about 7%, from about 0.5% to about 6%, from about 1% to about 6%, or from about 2% to about 6% by weight, relative to the total weight of the composition, including all ranges and subranges thereof. In some embodiments, the compositions according to the present disclosure comprise tannic acid in an amount of about 1% by weight, relative to the total weight of the composition.

Polysaccharide Gums

Compositions according to the disclosure comprise at least one polysaccharide gum. In various embodiments, suitable polysaccharide gums may be anionic gums and/or non-ionic.

Non-limiting examples of polysaccharide gums include acacia, agar, algin, alginic acid, ammonium alginate, amylopectin, calcium alginate, calcium carrageenan, carnitine, carrageenan, dextrin, gelatin, gellan gum, guar gum, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, dehydroxanthan gum, carrageenan gum, and biosacharide gum. Modified gums or derivatives of gums may also be used, such as, for example, deacylated gellan gum, welan gum, or hydroxypropylated guar gum, such as Jaguar HP 105 sold by Rhodia.

In some embodiments, suitable polysaccharide thickening agents that can be used are chosen from gums, such as gum arabic, tragacanth gum, karaya gum, guar gum, gellan gum, tara gum, locust bean gum, tamarind gum, xanthan gum, dehydroxanthan gum, carrageenan gum, Seneca gum, sclerotium gum, gellan gum, etc. In various embodiments, the polysaccharide may comprise, consist essentially of, or consist of sclerotium gum.

In various exemplary embodiments, the total amount of polysaccharide gum(s) may vary, or combinations thereof, typically ranges from about 0.1% to about 2% by weight, including all subranges therebetween, such as from about 0.1% to about 1.5%, from about 0.1% to about 1%, from about 0.1% to about 0.8%, from about 0.1% to about 0.5%, from about 0.5% to about 2%, from about 0.5% to about 1% by weight, relative to the total weight of the composition, including all ranges and subranges thereof. For example, in certain embodiments, the compositions comprise sclerotium gum, present in an amount ranging from about 0.1% to about 2% by weight, including all subranges therebetween, such as from about 0.1% to about 1.5%, from about 0.1% to about 1%, from about 0.1% to about 0.8%, from about 0.1% to about 0.5%, from about 0.5% to about 2%, from about 0.5% to about 1% by weight, relative to the total weight of the composition, including all ranges and subranges thereof.

Polymeric Emulsifiers

Compositions according to the disclosure comprise at least one polymeric emulsifier. In some embodiments, compositions disclosed herein are free or substantially free of monomeric emulsifiers.

Non-limiting examples of polymeric emulsifiers that can be chosen include carboxylic acid polymers which are crosslinked compounds containing one or more monomers derived from acrylic acid, substituted acrylic acids, and salts and derivatives of these acrylic acids and substituted acrylic acids, such as crosslinked homopolymers of an acrylic acid or of a derivative thereof, e.g. acrylamidopropylsulfonic acid, or crosslinked copolymers having (i) a first monomer selected from the group consisting of (meth)acrylic acid, derivatives thereof, short chain (e.g. C1-C4) acrylate ester monomers, and mixtures thereof, and (ii) a second monomer which is a long chain (e.g. C8-C40) substituted polyethylene glycol acrylate ester monomer. Other non-limiting examples of emulsifiers include ethylene oxide/propylene oxide block copolymers; alkylpolyglucosides; phospholipids; polyethoxylated ester of hydrogenated castor oil available commercially for example under the trade name Arlacel 989 (ICI); anionic emulsifiers such as fatty acid soaps e.g., potassium stearate and fatty acid sulphates e.g., sodium cetostearyl sulphate available commercially under the trade name Dehydag (Henkel); ethoxylated fatty alcohols, for example the emulsifiers available commercially under the trade name Brij (ICI); ethoxylated mono-, di-, and triglycerides, for example the emulsifiers available commercially under the trade name Labrafil (Alfa Chem.); certain methylglucose esters such as polyglycerol-3 methyl glucose distearate available commercially under the name Tegocare 450 (Degussa Goldschmidt); polyacrylamide emulsifier systems, acryloyldimethyltaurate polymeric emulsifiers such as those comprising acrylamide/sodium acryloyldimethyltaurate copolymer or mixtures thereof.

In some embodiments, compositions according to the present disclosure include polyacrylamide. In some embodiments, the at least one polymeric emulsifier comprises a crosslinked anionic copolymer of acrylamide and of AMPS, e.g. in the form of a water-in-oil emulsion, such as those sold under the name SEPIGEL 305 (INCI name: Polyacrylamide/C13-14 Isoparaffin/Laureth-7), or an acryloyldimethyltaurate polymer such as Acrylamide/Sodium acryloyldimethyltaurate copolymer, sold under the name SIMULGEL 600, Acrylamide/Sodium acryloyldimethyltaurate copolymer/Isohexa-decane/Polysorbate 80 by SEPPIC.

In various embodiment, the total amount of polymeric emulsifier(s) in the composition may range from about 0.1% to about 10% by weight, including all ranges and subranges thereof, such as, for example, from about 0.1% to about 9%, from 0.1% to about 8%, from 0.1% to about 7%, from 0.1% to about 6%, from 0.1% to about 5%, from about 0.1% to about 4%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4% by weight, based on the total weight of the composition.

Glyceryl Polyacrylate

Compositions according to the disclosure comprise glyceryl polyacrylate. In various embodiments, the total amount of glyceryl polyacrylate ranges from about 0.01% to about 1% by weight, including all ranges and subranges thereof, such as, for example, relative to the total weight of the composition. For example, in various embodiments, the compositions comprise glyceryl polyacrylate in an amount ranging from about 0.05% to about 1%, from about 0.05% to about 0.8%, from 0.05% to about 0.5%, from 0.1% to about 1%, from 0.1% to about 0.8%, from about 0.1% to about 0.6%, from about 0.1% to about 0.5%, from about 0.1% to about 0.4% by weight, based on the total weight of the composition.

In various embodiments, the amounts of the at least one polyphenol and glyceryl polyacrylate included in the composition may be chosen to provide optimum styling benefits. For example, the amounts of polyphenols and glyceryl polyacrylate may be chosen so as to have a weight ratio of polyphenol(s):glyceryl polyacrylate ranging from about 3:1 to about 10:1, for example, from about 3:1 to about 8:1.

Water

Compositions according to the disclosure comprise water. In various embodiments, the total amount of water is at least 70% by weight, such as from about 70% to about 96%, from about 80% to about 95%, from about 85% to about 95% by weight, relative to the total weight of the composition.

Latex Type Film Former

Compositions according to the disclosure may optionally comprise at least one latex type film former chosen acrylate-based polymers, polyurethane-based polymers, derivatives thereof, or combinations thereof. As used herein, polyurethane-based polymers and/or derivatives thereof are polymers contain carbamate linkages.

In some embodiments, acrylate-based polymers or derivatives used as latex type film formers may be chosen from acrylates copolymer, styrene/acrylates copolymer, acrylates/ethylhexyl acrylate copolymer, or mixtures thereof. In some instances, at least one latex type film former is acrylates copolymer, i.e., copolymers of two or more monomers consisting of acrylic acid, methacrylic acid or one of their simple esters. As used herein, acrylate-based polymers and derivatives thereof are polymers produced by polymerization of acrylic acid/esters, and/or various salts thereof.

In certain embodiments, the at least one latex type film former is chosen from polymers resulting from copolymerization of monomers chosen from (meth)acrylics, (meth) acrylates, and/or (meth)acrylamides. The term "(meth) acryl" and variations thereof, as used herein, means acryl or methacryl. In certain embodiments, the (meth)acrylic monomers may be chosen from acrylic acid, methacrylic acid, citraconic acid, itaconic acid, maleic acid, fumaric acid, crotonic acid, maleic anhydride, or mixtures thereof.

In certain embodiments, the (meth)acrylic monomers may be chosen from C1-C8 alkyl (meth)acrylic, methyl (meth) acrylic, ethyl (meth)acrylic, propyl (meth)acrylic, isopropyl (meth)acrylic, butyl (meth)acrylic, tert-butyl (meth)acrylic, pentyl(meth) acrylic, isopentyl (meth)acrylic, neopentyl (meth)acrylic, hexyl (meth)acrylic, isohexyl (meth)acrylic, 2-ethylhexyl (meth)acrylic, cyclohexyl (meth)acrylic, isohexyl (meth)acrylic, heptyl (meth)acrylic, isoheptyl (meth) acrylic, octyl (meth)acrylic, isooctyl (meth)acrylic, or mixtures thereof.

In certain embodiments, suitable acrylate-based polymers may be chosen from aqueous dispersions of Methacrylic Acid/Ethyl Acrylate copolymer (INCI name: Acrylates Copolymer, such as LUVIFLEX Soft sold by the company BASF), PEG/PPG-23/6 Dimethicone Citraconate/C10-30 Alkyl PEG-25 Methacrylate/Acrylic Acid/Methacrylic Acid/Ethyl Acrylate/Trimethylolpropane PEG-15 Triacrylate copolymer (INCI name: Polyacrylate-2 Crosspolymer, such as FIXATE Superhold sold by the company Lubrizol), Butyl acrylate, PEG-10 acrylate, PPG-6 acrylate and dimethylacrylamide copolymer (INCI name: Polyacrylate-3 crosspolymer), Styrene/Acrylic copolymer (such as NEOCRYL A-1120 sold by the company DSM), Ethylhexyl Acrylate/Methyl Methacrylate/Butyl Acrylate/Acrylic Acid/ Methacrylic Acid copolymer (INCI name: Acrylates/ Ethylhexyl Acrylate Copolymer, such as DAITOSOL 5000SJ sold by the company Daito Kasei Kogyo), Acrylic/ Acrylates Copolymer (INCI name: Acrylates Copolymer, such as DAITOSOL 5000AD sold by the company Daito Kasei Kogyo), or Acrylic copolymers and Acrylates Copolymers (such as VINYSOL 2140 sold by the company Daido Chemical, ACULYN 33 sold by the company Dow Chemical, LUVIMER MAE sold by the company BASF, or BALANCE CR sold by the company Akzo Nobel).

In various embodiments, the amount of latex type film former(s) chosen from acrylate-based polymers, polyurethane-based polymers, derivatives thereof, or combinations thereof, if present, may range up to about 10% by weight, including all subranges therebetween, such as, for example, from about 0.1% to about 10%, from about 0.1% to about 9%, from about 0.1% to about 8%, from about 0.1% to about 7%, from about 0.1% to about 6%, from about 0.1% to about 5%, from about 0.1% to about 4%, from about 0.1% to about 3%, from about 0.5% to about 10%, from about 0.5% to about 9%, from about 0.5% to about 8%, from about 0.5% to about 7%, from about 0.5% to about 6%, from about 0.5% to about 5%, from about 0.5% to about 4%, from about 0.5% to about 3%, from about 1% to about 10%, from about 1% to about 9%, from about 1% to about 8%, from about 1% to about 7%, from about 1% to about 6%, from about 1% to about 5%, from about 1% to about 4%, from about 1% to about 3%, from about 1.5% to about 10%, from about 1.5% to about 9%, from about 1.5% to about 8%, from about 1.5% to about 7%, from about 1.5% to about 6%, from about 1.5% to about 5%, from about 1.5% to about 4%, or from about 1.5% to about 3% by weight, relative to the total weight of the composition. In some embodiments, composition disclosed herein comprise acrylates copolymer in an amount ranging from about 0.1% to about 10%, such as from about 0.5% to about 10%, or from about 1% to about 10% by weight, such as about 0.5%, 1%, 1.5%, or 2% by weight, relative to the total weight of the composition.

Vegetable Oils

Compositions according to the disclosure may optionally comprise at least one vegetable oil. Suitable vegetable oils may be chosen from coconut oil, olive oil, castor seed oil, butyrospermum Parkii (Shea) butter, soybean oil, canola oil, rapeseed oil, corn oil, cottonseed oil, palm oil, peanut oil, safflower oil, sesame oil, sunflower oil, linseed oil, palm kernel oil, tung oil, jatropha oil, mustard oil, camelina oil, pennycress oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, walnut oil, or mixtures thereof.

In certain embodiments, if vegetable oil(s) are present, the total amount of vegetable oil(s) in a composition disclosed herein may range from about from about 1% to about 20% by weight, including all subranges therebetween, such as, for example, from about 1% to about 10%, or about 1% to about 6% by weight, relative to the total weight of the composition.

Humectants

Compositions according to the disclosure may optionally comprise at least one humectant. In certain embodiments, compositions according to the disclosure comprise at least two humectants.

Non-limiting humectant compounds that can be chosen include, for example, polyhydric alcohols, such as C2-C8 or C3-C6 polyhydric alcohols. By way of example, glycerol (glycerin), propylene glycol, butylene glycol, pentylene glycol, hexylene glycol, dipropylene glycol, diethylene glycol, and diglycerol may be chosen.

Additional non-limiting examples of humectants that can be chosen include hyaluronic acid, sugars such as sorbitol or xylitol, or beta-fructans, for example inulin. Mixtures of two or more humectants can also be chosen.

If present, the at least one humectant may be chosen from sorbitol, sorbitol glycerin, glycerin, propylene glycol, butylene glycol, pentylene glycol, hexylene glycol, dipropylene glycol, diethylene glycol, diglycerol, hyaluronic acid, xylitol, inulin, or mixtures thereof. In certain embodiments, the composition comprises at least one humectant in an amount ranging from about 0.1% to about 10% by weight, such as, for example, such as, for example, from about 0.2% to about 8%, from about 0.2% to about 5%, or from about 0.2% to about 1% by weight, relative to the total weight of the composition.

Ester Other than Glyceryl Polyacrylate

Compositions according to the disclosure may optionally comprise at least one ester other than glyceryl polyacrylate.

Glyceryl Esters (Glycerol Esters)

In some embodiments, compositions according to the disclosure comprise at least one glyceryl (or glycerol) ester or derivative thereof, other than glyceryl polyacrylate.

The at least one glyceryl ester may have a carbon chain of 8 to 24 carbons, and may be chosen from: i) esters of an oligomeric glycerol; ii) the arachidyl propionate sold under the trade mark WAXENOL 801 by Alzo; iii) phytosterol esters, triglycerides of fatty acids and derivatives thereof, such as hydrogenated cocoglycerides; iv) noncrosslinked polyesters resulting from the poly condensation between a linear or branched C4-C50 dicarboxylic acid or polycarboxylic acid and a C2-C50 diol or polyol; v) aliphatic esters of an ester resulting from the esterification of an aliphatic hydroxycarboxylic acid ester with an aliphatic carboxylic acid; or vi) a mixture thereof.

Non-limiting examples of the esters of an oligomeric glycerol include diglycerol, such as the condensates of adipic acid and of glycerol, for which a portion of the hydroxyl groups of the glycerols have reacted with a mixture of fatty acids, such as steric acid, capric acid, stearic and isostearic acid, and 12-hydroxystearic acid, such as those sold under the trade mark SOFTISAN 649 by the company Cremer Oleo or under the trademark SP SUPERMOL B MBAL-SS-(RB) by the company Croda, such as bis-diglyceryl polyacyladipate-2, or may be bis-diglyceryl polyacyladipate-1.

In certain exemplary embodiments, the glycerol esters may be polyglycerol esters of fatty acids (polyglyceryl esters) having a structure in accordance with the following formula (1):

(I)

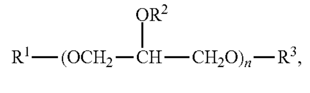

wherein n is from 2 to 20, from 2 to 10, or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$.

Non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, and polyglyceryl-10 stearate.

In some embodiments, at least one glyceryl ester is chosen from esters of an oligomeric glycerol, arachidyl propionate, phytosterol esters, triglycerides of fatty acids and derivatives thereof, noncrosslinked polyesters resulting from the poly condensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid, and a mixture thereof. Non-limiting examples of glyceryl esters include bis-diglyceryl polyacyladipate-1, bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or a mixture thereof. In some embodiments, the at least one emulsifier is chosen from glyceryl stearate, bis-diglyceryl polyacyladipate-1, bis-diglyceryl polyacyladipate-2, or a mixture thereof. In another embodiment, at least one emulsifier is chosen from glyceryl esters comprising bis-diglyceryl polyacyladipate-1 and/or bis-diglyceryl polyacyladipate-2, and optionally, a second glyceryl ester. In one other embodiment, the at least one emulsifier comprises a glyceryl ester that is glyceryl stearate, and optionally, a second glyceryl ester. In a preferred embodiment, the composition comprises bis-diglyceryl polyacryladipate-1 and/or bis-diglyceryl polyacryladipate-2, and optionally at least one additional ester other than glyceryl polyacrylate.

In various embodiments, the total amount of glyceryl ester(s) other than glyceryl polyacrylate, if present, may range from about 0.1% to about 5% by weight, including all subranges therebetween, such as, for example, from about 0.1% to about 3%, from about 0.1% to about 2%, from about 0.1% to about 1%, from about 0.2 to about 3%, from about 0.2% to about 2%, or from about 0.2% to about 1% by weight, relative to the total weight of the composition.

Non-Glyceryl Esters

In some embodiments, compositions according to the disclosure may also include a non-glyceryl ester. In some cases, the non-glyceryl ester other than glyceryl ester is chosen from isopropyl esters, cetyl esters, or a mixture thereof. Non-limiting examples of isopropyl esters include isopropyl myristate, isopropyl laurate, isopropyl oleate, isopropyl palmitate, and isopropyl stearate. In some embodiments, the ester that is not a glyceryl ester may be chosen from isopropyl myristate, cetyl esters, isopropyl palmitate, or a mixture thereof.

The ester other than glyceryl ester may also be chosen from a fatty ester. Non-limiting examples of fatty esters may include ethoxylated fatty esters, such as the adducts of ethylene oxide with esters of lauric acid, palmitic acid, stearic acid or behenic acid, and mixtures thereof. Exemplary suitable fatty esters may include those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

The glyceryl esters may, in some embodiments, have a carbon chain of 8 to 24 carbons. Non-limiting examples of glyceryl esters include bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or mixtures thereof.

In various embodiments, the total amount of ester(s) other than glyceryl polyacrylate, if present, may range from about 0.1% to about 5% by weight, including all subranges therebetween, such as, for example, from about 0.1% to about 3%, from about 0.1% to about 2%, from about 0.1% to about 1%, from about 0.2 to about 3%, from about 0.2% to about 2%, or from about 0.2% to about 1% by weight, relative to the total weight of the composition.

Additional Components

Compositions according to the disclosure may optionally comprise one or more additional components suitable for use in such compositions. Non-limiting examples of such additional components are provided below.

pH Adjusters

Compositions disclosed herein may include one or more pH adjusters to increase or decrease the overall pH of the composition. For example, one or more acids may be included to decrease the pH of the cosmetic composition. Examples of suitable acids for decreasing the pH of the compositions may include one or more acids. The cosmetic composition may include one or more bases, such as sodium hydroxide, potassium hydroxide and the like, to increase the pH of the cosmetic composition. Additional or alternative acids and bases that are suitable for adjusting the pH of the compositions are readily known to one of ordinary skill in the art. For instance, In some embodiments, the pH adjuster is sodium hydroxide solution such as 0.1M NaOH.

The amount of the pH adjuster in the compositions may be based on the desired pH of the final composition and/or product for improving curl definition, curl regularity, and/or curl elongation. For example, the total amount of the pH adjuster may range from about 0.0001% to about 10% by weight, including ranges and sub-ranges therebetween, based on the total weight of the cosmetic composition.

Preservatives

One or more preservatives may be included in the compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, benzoic acid, chlorhexidine digluconate, ethylenediamine-tetraacetic acid (EDTA), potassium sorbate, and/or grapefruit seed extract, or a mixture thereof. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, Vitamin E (tocopherol), or mixtures thereof. In some cases, the hair-treatment compositions may include one or more preservatives selected from the group consisting of sodium benzoate, benzoic acid, chlorhexidine digluconate, chlorhexidine dihydrochloride, salicylic acid, phenoxyethanol, methyl paraben, or mixtures thereof.

The total amount of the one or more preservatives, when present, may vary. In some cases, the total amount of the one or more preservatives may range from about 0.01% to about 5%, from about 0.01% to about 4%, from about 0.01% to about 2%, from about or about 0.01% to about 3% by weight, relative to the total weight of the composition.

Auxiliary Components

Compositions according to the disclosure may optionally comprise any auxiliary component suitable for use in such compositions. Such components may include, but are not limited to, dyes/pigments for adding color to the composition, moisturizing agents, fatty substances, thickeners other than those previously described, fillers, structuring agents, shine agents, antioxidants or penetrants, sequestrants, fragrances, buffers, dispersants, plant extracts, such as apricot seed powder, opacifiers, sunscreen agents, vitamins, and antistatic agents.

Optional auxiliary components may be present in an amount ranging up to about 15%, such as from about 0.001% to about 10%, from about 0.01% to about 5%, or from about 0.01% to about 1% by weight, relative to the total weight of the composition.

In various embodiments, the compositions are acidic and may have a pH of less than 7. For example, the pH of the composition may range from about 3 to about 7, such as from about 3.5 to about 6.8, from about 3.5 to about 6.5, from about 3.5 to about 6, from about 3.5 to about 5.5, from about 3.5 to about 5, from about 3.5 to about 4.5, or from about 4 to about 6, including all ranges and subranges therebetween.

In some embodiments, the hair styling compositions according to the present disclosure do not include a chemical relaxing agent. Additionally, the compositions disclosed herein may optionally not include a cationic polymer. The compositions disclosed here may also be free or essentially free of dyes, pigments, and/or colorants.

Compositions according to the disclosure may be rinse-off compositions or leave-in compositions, and are typically in the form of a liquid, cream, or lotion, but are not so limited. In some embodiments, the compositions are a non-aerosol type product, which may be dispensed from a bottle, tube, or spray-bottle.

In some embodiments, the compositions may be a hair treatment or conditioner product, a hair styling product, or a product that styles hair while providing treatment and/or conditioning benefits.

II. Methods

The compositions disclosed herein can be used for styling hair, in particular, for temporarily straightening curly or wavy hair. In addition, the compositions disclosed herein are surprisingly capable of providing a variety of additional desirable sensory properties, for example, anti-frizz, moisture, smoothness, softness, and/or shine to the hair. As such, the present disclosure also relates to methods for styling hair, particularly, temporarily straightening curly or wavy hair, while at the same time, caring for and conditioning hair, and/or imparting one or more above-described sensory benefits to the hair.

Methods according to the disclosure typically include applying an effective amount of a composition disclosed herein to hair having waves or curls, and straightening. As used herein, the term "effective amount" refers to an amount sufficient to provide a desired straightening effect to the hair, taking into account the degree of curliness, the length, the volume, and the texture of the hair, and/or an amount sufficient to provide a desired sensory benefit to the hair. In general, from about 0.5 grams to about 50 grams of product is applied to the hair, depending on the specific product formulation, hair length, hair volume, and hair style type. The composition applied to the hair may, for example, be distributed evenly by combing through with fingers or a means such as a comb or the like. After the composition is evenly distributed on the hair, the hair is allowed to air dry under an ambient condition for a period of time as needed, such as, for example, at least 15 minutes, at least 30 minutes, at least 1 hours, or up to 6 hours, until the hair is dried. In certain circumstance, instead of allowing the hair to air dry under an ambient condition, the hair may be dried with a rollerball dryer or a blow dryer on a cool setting, for example, at a temperature lower than 50° C., such as 40-45° C. After the hair is dried, the hair is combed with fingers (i.e., running fingers through the hair) or by using a comb or the like, to break the film or coating formed by the compositions on the hair for straightening the hair, and/or for a less stiff and more natural movement. Typically, no heat or chemical relaxers are applied to the hair before, during, or after the styling composition is applied to the hair.

The composition may be allowed to remain on the hair as a leave-in product for any period of time as needed, for example, a few hours or a few days, or until the next washing or rinsing of the hair. The composition applied on the hair can be allowed to remain on the hair overnight or for any desired period of time, until next washing the hair.

In some embodiments, before applying the composition to the hair, the hair may be first cleansed with a commercially available shampoo, and/or rinsed with water. The composition may then be applied to the washed and/or rinsed hair, preferably when the hair is wet, damp, or moist. In some other embodiments, before applying the composition to the hair, if the hair is dry, the hair may optionally be moistened, damped, or wetted by water spray or using a wet towel.

Methods according to the disclosure generally do not require the use of a reducing agent, including a base, in particular a strong base (as in lye-based and no lye relaxers that employ a metal hydroxide), or heating the hair in order to achieve a temporary straightening effect. As such, in some embodiments, the method does not include using a chemical relaxing agent, a reducing agent or a base, and/or does not including heating the hair.

In various embodiments, the methods of treating hair with the compositions according to the disclosure impart the benefits described above to the hair, without a greasy feel or flaking, relative to hair not having been treated with a composition according to the disclosure. The benefits imparted to the hair may remain a desired length of time, such as a few hours, a few days, or until the hair is rinsed or washed.

The compositions described herein are not mascara compositions, i.e. are not intended to be applied to eyelashes and/or eyebrows. The compositions are likewise not makeup compositions, i.e. are not intended to be applied to skin, in particular, to skin on the face, body, or lips. Thus, treatment of, or application to, the hair is intended to be limited to hair on the head, i.e. the scalp of the head, and not eyelashes, eyebrows, body or facial hair, or the like. In such embodiments, a skilled person understands that "hair on the head" means hair that grows from the scalp of the head, and excludes eyebrows, eyelashes, facial hair, etc.

Having described the many embodiments of the present invention in detail, it will be apparent that modifications and variations are possible without departing from the scope of the disclosure defined in the appended claims. Furthermore, it should be appreciated that all examples in the present disclosure, while illustrating many embodiments of the disclosure, are provided as non-limiting examples and are, therefore, not to be taken as limiting the various aspects so illustrated. It is to be understood that all definitions herein are provided for the present disclosure only.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the compositions.

In this application, the use of the singular includes the plural unless specifically stated otherwise. The singular forms "a," "an," "the," and "at least one" are understood to encompass the plural as well as the singular unless the context clearly dictates otherwise, and these expressions, as well as the expression "one or more" which means "at least one," are expressly intended to include the individual components as well as mixtures/combinations thereof. Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, or F may be included, one or more of a salt of A, a salt of B, a salt of C, a salt of D, a salt of E, or a salt of F may be included, or a mixture of any two of A, B, C, D, E, F, a salt of A, a salt of B, a salt of C, a salt of D, a salt of E, and a salt of F may be included. However, it is to be understood that such language also includes embodiments where G, H, I, etc., are present, as long as at least one of A, B, C, D, E, F, or a salt thereof, is also present.

The term "and/or" should be understood to include both the conjunctive and the disjunctive. For example, "A and/or B" means "A and B" as well as "A or B," and expressly covers instances of either without reference to the other. For example, a composition that comprises "an emulsifier chosen from fatty alcohols and/or esters" means that the disclosure includes compositions comprising one or more fatty alcohols or one or more esters, as well as compositions comprising one or more fatty alcohols and one or more esters. As a further example, disclosure of "methods of styling the hair, straightening the hair, and/or reducing frizz of the hair" includes methods of styling the hair or methods of straightening the hair or methods of reducing frizz of the hair, as well as methods of styling the hair and straightening the hair, methods of styling the hair and reducing frizz of the hair, methods of styling the hair and straightening the hair and reducing frizz of the hair, etc.

As used herein, the phrases "and mixtures thereof," "and a mixture thereof," "and combinations thereof," "and a combination thereof," "or mixtures thereof," "or a mixture thereof," "or combinations thereof," "or a combination thereof," and variations thereof are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

For purposes of the present disclosure, it should be noted that to provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value. All ranges and amounts given herein are intended to include sub-ranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. The term "about" is used herein to indicate a difference of up to +/−10% from the stated number, such as +/−9%, +/−8%, +/−7%, +/−6%, +/−5%, +/−4%, +/−3%, +/−2%, or +/−1%. Likewise, all endpoints of ranges are understood to be individually disclosed, such that, for example, a range of 1:2 to 2:1 is understood to disclose a ratio of both 1:2 and 2:1.

Further, unless expressly stated otherwise or when the context of the disclosure clearly dictates otherwise, the language "the at least one X may be present in an amount ranging from Y % to Z %" is to be understood to mean that the total amount of X's present in the composition ranges from Y % to Z %, inclusive of the endpoints. For example, "the at least one polyphenol may be present in an amount ranging from about 0.01% to about 10%" means that the total amount of polyphenols present ranges from about 0.01% to about 10%, inclusive of both 0.01% and 10%.

"Active material" as used herein with respect to the percent amount of an ingredient or raw material, refers to 100% activity of the ingredient or raw material.

All amounts given herein are relative to the amount of active material, unless otherwise indicated.

Unless otherwise indicated, all percentages herein are by weight, relative to the total weight of the composition.

All percentages, parts and ratios herein are based upon the total weight of the compositions of the present disclosure, unless otherwise indicated.

As used herein, the term "treat" (and its grammatical variations, such as "treating") refers to the application of the compositions of the present disclosure onto the surface of the hair on the head.

As used herein, the phrase "applying a composition onto hair," and variations thereof is intended to mean contacting the hair, with at least one of the compositions of the disclosure, in any manner. It may also mean contacting the hair in an effective amount.

As used herein, the term "styling" is intended to include "shaping" and "straightening."

As used herein, the term "curly hair" refers to any hair including a curl, and "wavy hair" refers to any hair including a wave. The curl and/or wave may be natural or unnatural, i.e., formed by chemical treatment or physical treatment of the hair. The degree of curliness and/or waviness of the hair may vary and is not limited.

A "leave-in" composition or product refers to a hair-treatment composition that is not rinsed and/or washed away with water or acceptable solvent after the application of the composition onto the hair; instead, the composition is allowed to remain on the hair for a period of time as desired, such from 1 hour, 2 hours, 3 hours, 4 hours, up to 8 hours, overnight, or as long as needed, until next time of washing or rinsing the hair.

As used herein, the term "polyol" refers to an organic molecule comprising at least two free hydroxyl groups.

The terms "substantially without" or "essentially without" as used herein means the specific material may be used in a manufacturing process in small amounts that do not materially affect the basic and novel characteristics of the compositions according to the disclosure. The terms may also mean that the specific material is not used in a manufacturing process but may still be present in a raw material that is included in the composition.

As used herein, unless expressly stated otherwise, the term "substantially free" or "essentially free" means the specific material may be present in small amounts that do not materially affect the basic and novel characteristics of the compositions according to the disclosure. For instance, there may be less than 2% by weight of a specific material added to a composition, based on the total weight of the compositions (provided that an amount of less than 2% by weight does not materially affect the basic and novel characteristics of the compositions according to the disclosure. Similarly, the compositions may include less than 2%, less than 1.5%, less than 1%, less than 0.5%, less than 0.1%, less than 0.05%, or less than 0.01%, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure. The term "substantially free" or "essentially free" as used herein may also mean that the specific material is not added to the composition but may still be present in a raw material that is included in the composition.

As used herein, the term "salts" refers to throughout the disclosure may include salts having a counter-ion, in either ionized or un-ionized form. It is to be understood that, with regard to salts of acids described herein, it is intended to encompass the use of a salt of the acid as an ingredient added to a composition according to the disclosure, or to the salt of the acid that forms when the acid is used as an ingredient in a composition according to the disclosure (in ionized or un-ionized form).

As used herein, the term "synthetic" means a material that is not of natural origin. The term "natural" and "naturally-sourced" means a material of natural origin, such as derived from plants, which also cannot be subsequently chemically or physically modified. "Plant-based" means that the material came from a plant.

As used herein, the term "temporary" should be understood to indicate that some degree of benefit or effect is imparted to the hair that remains from when the hair is treated with a composition according to the disclosure, until the composition is removed from the hair, e.g. by washing the hair.

As used herein, the term "heatless" or the phrase "without a use of heat," when being used in describing a process of straightening hair as disclosed herein, should be understood to indicate that no heating no heating tools, such as a hair heater, a flat heating plate, an iron, a steamer, a hair dryer set on high temperature, or the like, is used in the process disclosed herein. In some circumstance, in order to shorten the time needed to dry the hair, a hair dryer, for example, a rollerball, with setting of temperature slightly higher than room temperature but lower than 50° C., such as 40-45° C., may be used to dry the hair. In this situation, increasing the temperature of the hair to a temperature that is slightly higher than room temperature but lower than 50° C. is not considered providing or using heat.

Unless otherwise expressly stated, it is in no way intended that any method set forth herein be construed as requiring that its steps be performed in a specific order. Accordingly, where a method claim does not expressly recite an order to be followed by its steps or it is not specifically stated in the claims or descriptions that the steps are to be limited to a specific order, it is no way intended that any particular order be inferred.

EXAMPLES

The following examples are intended to be non-limiting and explanatory in nature only. In the Examples, amounts are expressed in percentage by weight (wt %) of active materials, relative to the total weight of the composition, unless otherwise noted.

Example 1—Compositions

The inventive and comparative compositions set forth in Table 1 were prepared according to the process described below.

TABLE 1

| | Comparative | | | Inventive | | | |
|---|---|---|---|---|---|---|---|
| INCI US | C1 | C2 | C3 | 1A | 1B | 1C | 1D |
| TANNIC ACID | 1.0 | 1.0 | 1.0 | 1.0 | 1.0 | 1.0 | 1.0 |
| POLYACRYLAMIDE | 0.6 | 0.6 | 0.6 | 0.6 | 0.6 | 1.2 | 1.2 |

TABLE 1-continued

| INCI US | Comparative C1 | C2 | C3 | Inventive 1A | 1B | 1C | 1D |
|---|---|---|---|---|---|---|---|
| GLYCERYL POLYACRYLATE | | 0.2 | | 0.2 | 0.2 | 0.2 | 0.2 |
| ACRYLATES COPOLYMER | | | 1.0 | 1.0 | 1.0 | | |
| SCLEROTIUM GUM | 0.25 | 0.25 | 0.25 | 0.25 | 0.25 | 0.25 | 0.25 |
| COCOS NUCIFERA (COCONUT) OIL | 1.5 | 1.5 | 1.5 | 1.5 | 1.5 | 1.0 | 1.0 |
| OLEA EUROPAEA (OLIVE) FRUIT OIL | 1.0 | 1.0 | 1.0 | 1.0 | 1.0 | 1.0 | 1.0 |
| RICINUS COMMUNIS (CASTOR) SEED OIL | 1.0 | 1.0 | 1.0 | 1.0 | 1.0 | | |
| BUTYROSPERMUM PARKII (SHEA) BUTTER | | | | | | 2 | 2 |
| HYDROGENATED STARCH HYDROLYSATE | 0.35 | 0.35 | 0.35 | 0.35 | 0.35 | | |
| ISOPROPYL MYRISTATE | 1.0 | 1.0 | 1.0 | 1.0 | 1.0 | | |
| GLYCERYL STEARATE | | | | | | | 0.5 |
| CETEARYL ALCOHOL | | | | | | | 0.37 |
| FRAGRANCE | 0.5 | 0.5 | 0.5 | 0.5 | | | |
| PRESERVATIVES AND PH ADJUSTER, STABILIZER | <1.7 | <1.7 | <1.7 | <1.7 | <1.7 | <1.7 | <1.7 |
| THYLHEXYLGLYCERIN, GLYCERIN | <2.5 | <2.5 | <2.5 | <2.5 | <2.5 | <2.5 | <2.5 |
| WATER AND NON-AQUEOUS SOLVENT | QS | QS | QS | QS | QS | QS | QS |

Preparation Process:

1) Add 75% of water to a main tank and heat the water to about 60-65° C.
2) Sprinkle gum in the heated water. Mix with a homogenizer using a rotor-stator blade for about 15 to about 20 minutes until the gum is fully dispersed.
3) After the gum was fully dispersed, add coconut oil, castor seed oil, olive oil, and isopropyl myristate to the main tank at 60-65° C.
4) Add acrylates copolymer (dilute in 20% water). Mix with a homogenizer using a rotor-stator blade for about 20 minutes until uniform.
5) Once the vegetable oils, isopropyl myristate, and acrylates copolymer are uniformly dispersed, cool the mixture to a temperature of about 25° C. to about 30° C.
6) After the mixture is cooled, add glyceryl polyacrylate to the main tank and mix with a propeller-type blade until uniform.
7) Add fragrance and mix until uniform.
8) Heat the content in the main tank to about 35° C. and add preservatives, mixing until uniform between additions.
9) Add hydrogenated starch hydrolysate in the main tank and mix until uniform.
10) Add polyacrylamide (and) c13-14 isoparaffin (and) laureth-7 (SEPIEL 305™) and mix until uniform. Batch will thicken.
11) Add buffers to adjust the pH of the mixture in the main tank to 3.5-4.5.
12) Add tannic acid (dilute in 5% water) and mix until uniform.

All compositions were in the form of oil-in-water emulsion and had pH of about 3.5 to about 4.5 at 25° C. The compositions had Brookfield viscosities of about 2440 cps, measured with a spindle B at 50 rpm for 1 minute under ambient conditions.

Example 2—Stability Study

The stabilities of exemplary inventive compositions 1 A and 1B were evaluated over a period of up to two months. The pH values of compositions 1A and 1B were respectively measured on the initial date (day 0) and the last days of the first week, the fourth week, and the eighth week after the initial date at room temperature (25° C.) and at elevated temperature (45° C.). The viscosities of compositions 1A and 1B were respectively measured on the initial date (day 0) and the last days of the fourth week and the eighth week after the initial date at room temperature (25° C.) and at elevated temperature (45° C.) using a Rheomat RM 180 viscometer and a Brookfield viscometer. The appearance of these compositions were also observed and evaluated for any onset of precipitation or separation, an indicator of instability, during this period of two months.

Table 2 shows the values of pH of compositions 1A and 1B measured over the two months at 25° C. and 45° C. Δ pH represents the change of pH values.

TABLE 2

| | Day 0 | 1week (25°/45° C.) | | 4 weeks (25° C./45° C.) | | 8 weeks (25° C./45° C.) | |
|---|---|---|---|---|---|---|---|
| Composition | pH | pH | Δ pH | pH | Δ pH | pH | Δ pH |
| 1A | 4.31 | 4.10 | 0.21 | 4.35 | −0.04 | 4.26 | 0.05 |
| | | 3.99 | 0.32 | 3.93 | 0.35 | 4.14 | 0.17 |

TABLE 2-continued

| | Day 0 | 1week (25°/45° C.) | | 4 weeks (25° C./45° C.) | | 8 weeks (25° C./45° C.) | |
|---|---|---|---|---|---|---|---|
| Composition | pH | pH | Δ pH | pH | Δ pH | pH | Δ pH |
| 1B | 4.36 | 4.10 | 0.26 | 4.08 | 0.28 | 4.10 | 0.26 |
| | | 4.00 | 0.36 | 3.81 | 0.55 | 3.96 | 0.30 |

Table 3 summaries the viscosities measured by a Rheomat RM 180 with spindle 3 for 30 seconds and the onset of any precipitation (PPT) or separation of compositions 1A and 1B measured and/or evaluated over the two months at 25° C. and 45° C. Δ η represents the change of the viscosities. The Rheomat viscosity of 35-50 DU corresponds to a Brookfield viscosity of about 2440 cps measured with a spindle B at 50 rpm.

TABLE 3

| | Day 0 | 4 weeks (25°C/45° C.) | | | 8 weeks (25°C/45° C.) | | |
|---|---|---|---|---|---|---|---|
| Composition | η (DU) | η (DU) | Δ η | PPT | η (DU) | Δ η | PPT |
| 1A | 43.7 | 44.5 | 0.8 | No | 42.6 | −0.9 | No |
| | | 48.9 | 5.2 | | 42.8 | −0.8 | |
| 1B | 35.6 | 38.7 | 3.1 | No | 38.4 | 2.8 | No |
| | | 40.0 | 4.4 | | 41.6 | 6.0 | |

As can be seen from Table 2 and Table 3, at the end of the study, no precipitation or phase separation was observed, and only nonsignificant minor changes in pH and viscosity were noted, and only a minor change in color was observed. The results demonstrate that compositions 1A and 1B were stable.

Example 3—In Vitro Hair Swatch Performance Testing

In vitro hair swatch testing was performed to evaluate the performance of inventive composition 1A in comparison with comparative compositions C1, C2, and C3, as well as water (control) on Caucasian hair swatches with natural curls.

The testing and evaluation were performed as described below. First, the hair swatches were washed with a commercially available rinse-out shampoo. After shampooing, excess water was squeezed out of the swatches. Next, equal amounts of compositions 1A, C1, C2, C3, and water were respectively applied to a separate hair swatch at a rate of about 0.15 g of composition per 1 g of hair. After then, ten passes with finger were made to the hair swatches to ensure that the compositions were evenly distributed on the hair, followed by three passes with a comb to comb the hair straight. After combing, the hair swatches were evaluated for the level of frizz and sensorial properties, and photographs of the hair swatches were taken (time point 1, T1). The hair swatches were then air dried at an ambient condition. During drying, the swatches were shaken five times to mimic consumer movement. After the hair was dried, ten finger passes were made to the hair swatches to break the film formed by the compositions on the hair fibers. After breaking the film, the hair was evaluated and rated for the straightness, frizz, and tactile properties, compared to the hair treated with water (control). Photographs of the hair swatches were also taken at this time point (T2). After the evaluation at T2, the swatches were placed in a humidity chamber having 80% relative humidity (RH) at room temperature (25° C.), 80% RH for one hour. The swatches were re-evaluated for straightness and frizz after exposure to the high humidity condition for 30 minutes and 1 hours. Photographs of these hair swatches were taken after one hour exposure in the condition of 80% relative humidity (RH) at room temperature (25° C.) (time point, T3). The above testing and evaluation were performed in duplicate, i.e., each composition was tested on two separated hair swatches, compared to two separate control hair swatches treated with water.

All property evaluations were independently performed by 13 individuals. The straightness was graded on a scale of 1-5, with 1 the most straight and 5 the least straight. The frizziness was also graded on a scale of 1-5, with 1 the least frizzy and 5 the frizziest.

The appearance of the hair swatches treated with compositions C1-C3 and 1A, compared to the control hair, at time points T1, T2, and T3 was illustrated in the photographs in FIG. 1. As can be seen in FIG. 1, while the hair swatches treated with comparative compositions C1-C3 were straighter and less frizzy than the control hair swatches, the hair treated with inventive composition 1A were the most straight and least frizzy. The straightening and frizz control benefits provided by composition 1A lasted even after the hair swatches were exposed to a condition having high humidity condition (80% RH) for one hour. Therefore, the straightening and frizz control benefits provided by composition 1A is lasting.

Figure 2:
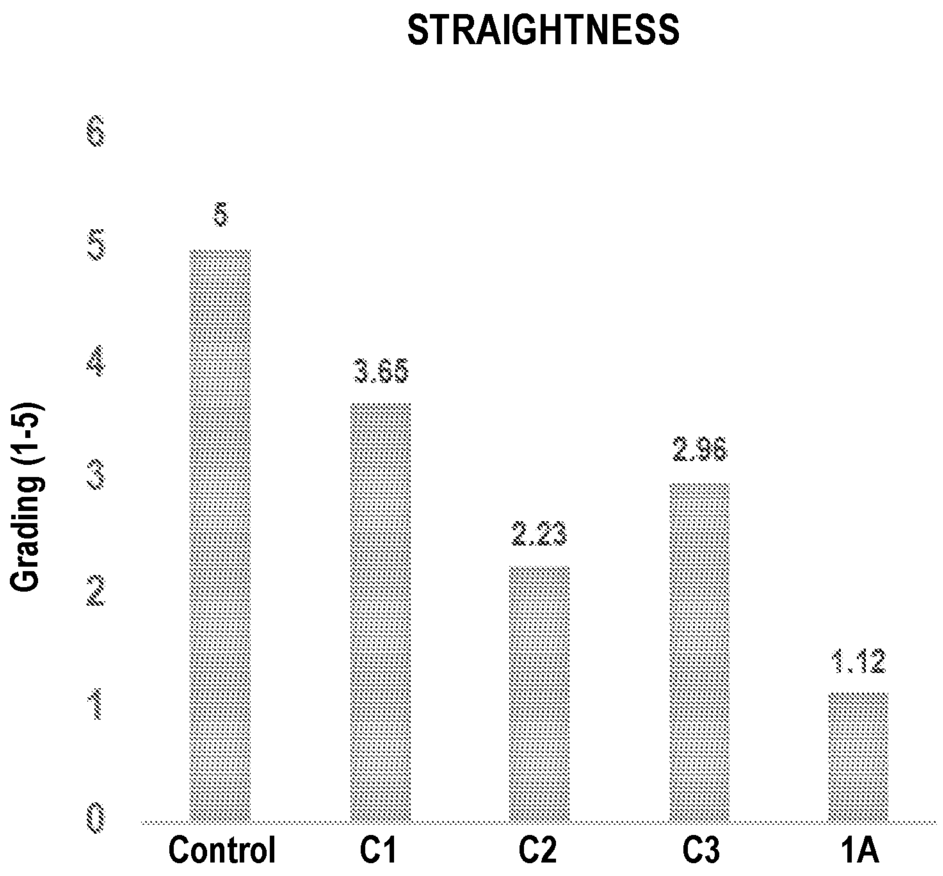
FIG. 2 is a graph showing the graded straightness of hair treated with composition 1A according to the present disclosure and comparative compositions C1-C3, compared to a control hair swatch treated with water, after being exposed to a condition having 80% relative humidity at room temperature for 1 hour (T3).
Figure 3:
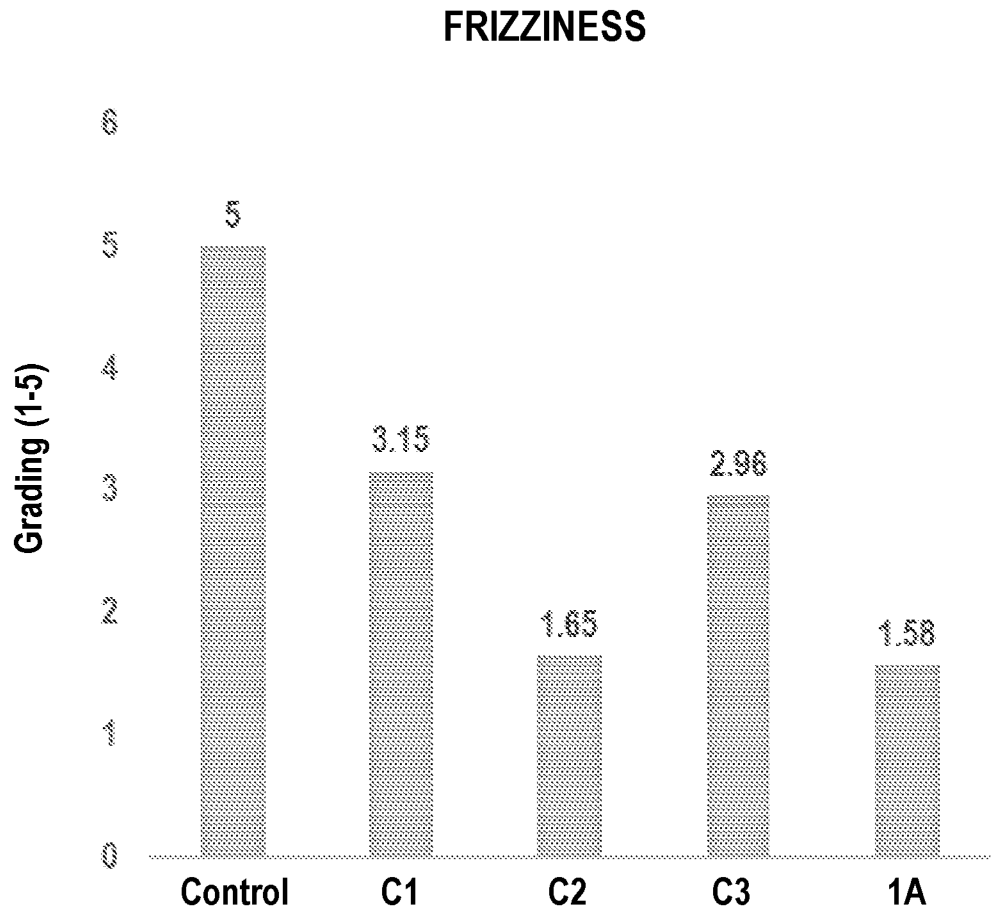
FIG. 3 is a graph showing the graded frizziness of hair treated with composition 1A and comparative compositions C1-C3, compared to control hair treated with water, after being exposed to a condition having 80% relative humidity at room temperature for 1 hour (T3).

The grading of straightness of the treated hair at time point T3, in comparison with control, was shown in Table 4 and FIG. 2. The grading of frizziness of the treated hair at time point T3, in comparison with control, was shown in Table 5 and FIG. 3. As can be seen in Tables 4 and 5 and FIGS. 2 and 3, inventive composition 1A significantly improved frizz control and straightness to the hair, compared to comparative compositions C1, C2, and C3.

TABLE 4

| Straightening | | | | | |
|---|---|---|---|---|---|
| Panelist | Ctrl Water | Set A C1 | Set B C2 | Set C C3 | Set D 1A |
| 1 | 5 | 4 | 3 | 3.5 | 2 |
| 2 | 5 | 4 | 2.5 | 3 | 1 |
| 3 | 5 | 4 | 2 | 3 | 1 |
| 4 | 5 | 4 | 3 | 2 | 1 |
| 5 | 5 | 4 | 2.5 | 3 | 1 |
| 6 | 5 | 2 | 2 | 3 | 1 |
| 7 | 5 | 4 | 2 | 3 | 1 |
| 8 | 5 | 4 | 2 | 3 | 1 |
| 9 | 5 | 4 | 2 | 3 | 1 |
| 10 | 5 | 3 | 2 | 4 | 1 |
| 11 | 5 | 3 | 2 | 3 | 1 |
| 12 | 5 | 3.5 | 2 | 2 | 1.5 |
| 13 | 5 | 4 | 2 | 3 | 1 |
| Average | 5 | 3.65 | 2.23 | 2.96 | 1.12 |

TABLE 5

| Frizziness | | | | | |
|---|---|---|---|---|---|
| Panelist | Ctrl water | Set A C1 | Set B C2 | Set C C3 | Set D 1A |
| 1 | 5 | 3 | 3 | 4 | 2 |
| 2 | 5 | 2.5 | 1 | 3 | 2 |
| 3 | 5 | 3 | 1 | 4 | 2 |
| 4 | 5 | 4 | 1 | 3 | 2 |
| 5 | 5 | 4 | 2.5 | 3 | 1 |
| 6 | 5 | 2 | 1 | 3 | 2 |
| 7 | 5 | 4 | 1 | 2 | 2 |
| 8 | 5 | 3 | 2 | 2 | 1 |
| 9 | 5 | 4 | 2 | 3 | 1 |
| 10 | 5 | 4 | 1 | 3 | 2 |
| 11 | 5 | 3 | 1 | 2 | 1 |
| 12 | 5 | 2.5 | 2 | 2.5 | 1.5 |
| 13 | 5 | 2 | 3 | 4 | 1 |
| Ave | 5 | 3.15 | 1.65 | 2.96 | 1.58 |

Example 4—In Vitro Mannequin Testing

The performance of compositions with and without fatty alcohols was evaluated on mannequin heads having curly hair. Compositions 1C and 1D were used in this testing.

photographs of the mannequin heads were taken to show the appearance of the hair at the initial time point (T0).

The mannequin heads were first washed by shampooing, conditioning, and rinsing. After the hair was washed, excess water was removed from the hair with a towel and the hair was detangled using a brush. After then, compositions 1C and 1D were respectively applied evenly in sections in an amount of about 5 g/half head on a separate mannequin head when the hair was detangled and still wet. After the application, compositions 1C and 1D were allowed to leave on the hair and the hair was combed to straighten and then dried with a rollerball at a temperature of about 40-45° C. for about 60 minutes.

The straightness and frizziness of the hair were evaluated by tactile assessment and visual observation before, during, and after the treatment. Photographs of the mannequin heads were taken to show the appearance of the hair before the hair was treated (initial time point, T0), when the hair was detangled and still wet after the application of the compositions (T1), and the final look of the treated hair when it was dried (T2). The Photographs of the mannequin heads were shown in FIG. 4.

Figure 4:
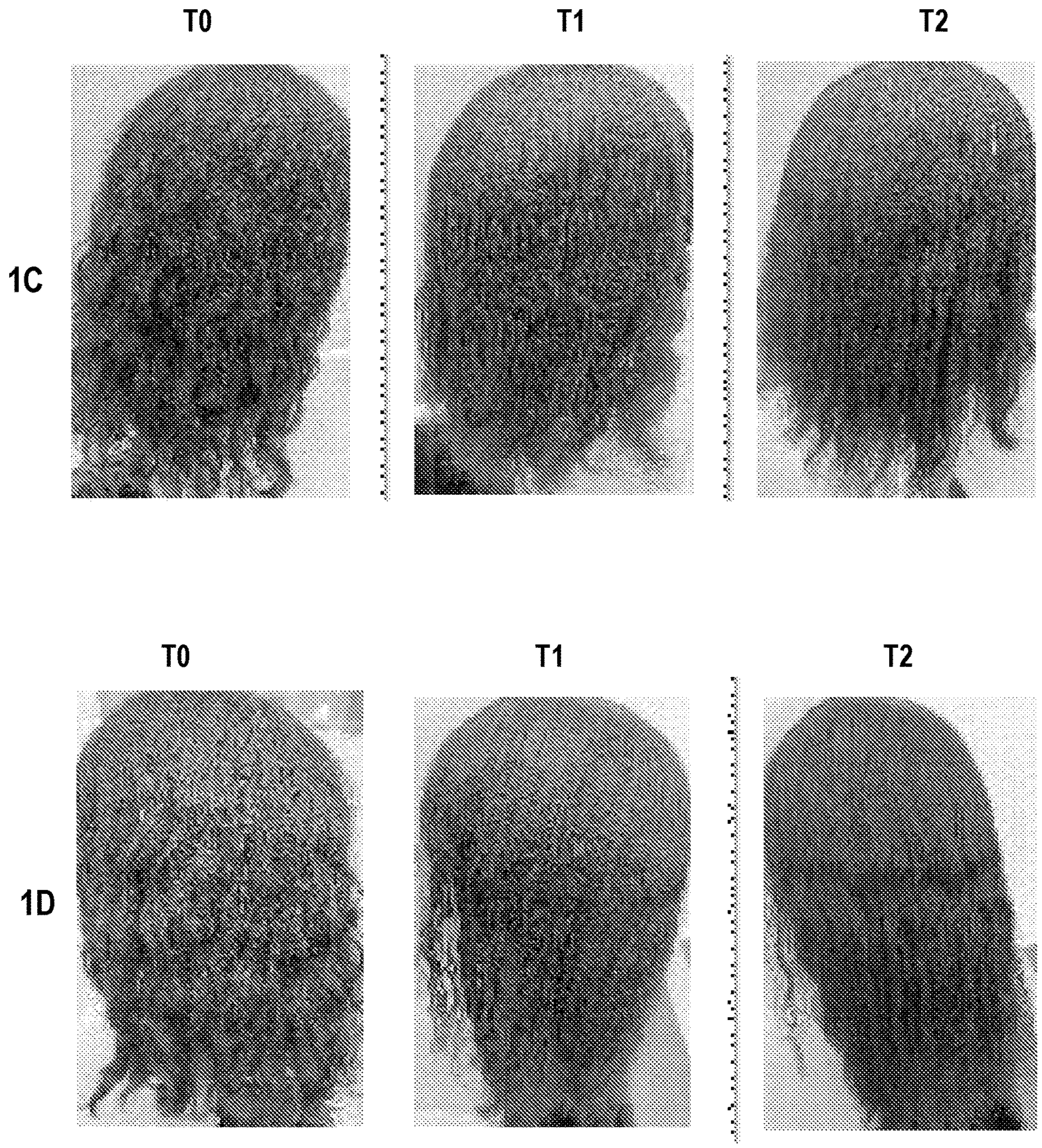
FIG. 4 is a set of photographs showing untreated mannequin heads (T0), mannequin heads after the hair was treated with composition 1C or composition 1D while the hair was still wet (T1), and mannequin heads after the hair treated with composition 1C or composition 1D was dried (T2).

As shown in FIG. 4, compositions 1C and 1D provided similar curl reduction to the hair. However, compared to the hair treated with composition 1D, which includes a fatty alcohol, the hair treated with composition 1C, which does not include fatty alcohols, had a cleaner and lighter appearance, and felt less coated (waxy).

Example 5—In Vivo Evaluation on Consumer Hair

The performance of composition 1A was tested on consumers having wavy to curly hair, with varying hair density (low-high), length (short-long), diameter (fine-coarse), and porosity/sensitivity (low-high).

Before application of composition 1A, the hair of the consumers was washed and conditioned with a commercially available shampoo and a commercially available lightweight conditioner. After excess water was removed from the hair and when the hair was still damp, composition 1A was applied on the hair of the consumers' through two different application routines. In the first application routine (routine 1), also called here a control routine or standard routine, composition 1A was applied on half head of a consumer's in sections, including root of the hair, like how a hair color or a conventional straightening composition is applied by a stylist, and was then evenly distributed on the hair by combing through the hair. In the second application routine (routine 2), i.e, a modified or new routine, composition 1A was applied on the other half head of the consumer's in a manner less focusing at root and less sectioning, like how a consumer usually does, and was then evenly distributed on the hair by coming through the hair. After the application, the hair was air dried for six hours. After the hair was dried, the hair was passed by fingers to break the film or coating formed on the hair. Before, during, and after the treatment, photographs of the hair were taken from back of the head, and tactile assessment and visual observation of the hair were performed by stylists.

Figure 5A:
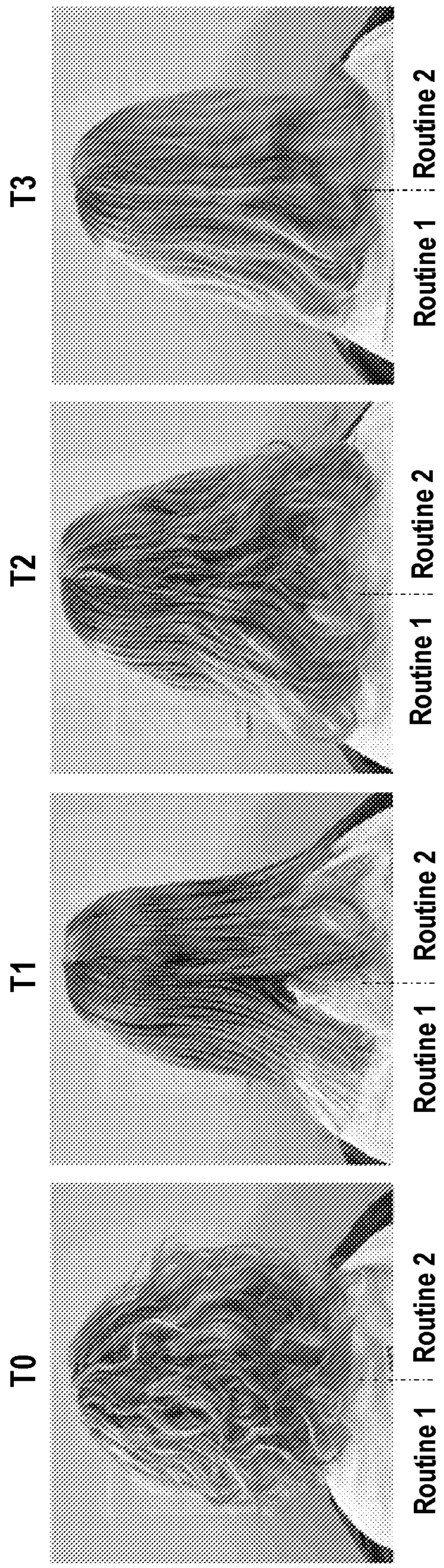
FIGS. 5A, 5B, and 5C are sets of photographs illustrating the appearance of three consumers' hair before the hair was treated (T0), after the hair was treated with composition 1A via a conventional application routine (Routine 1) (left) and a new routine (Routine 2, right), respectively, while the hair was wet (T1), after the hair was dried and before breaking the film on the hair (T2), and after breaking the film on the hair (T3).
Figure 5B:
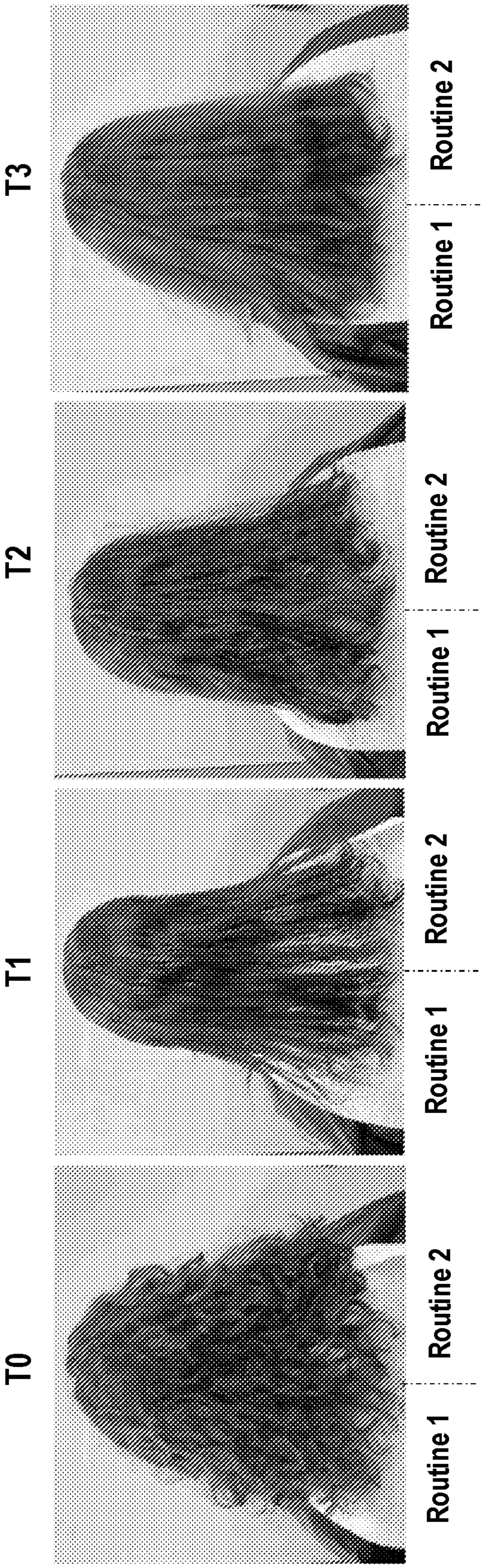
Figure 5C:
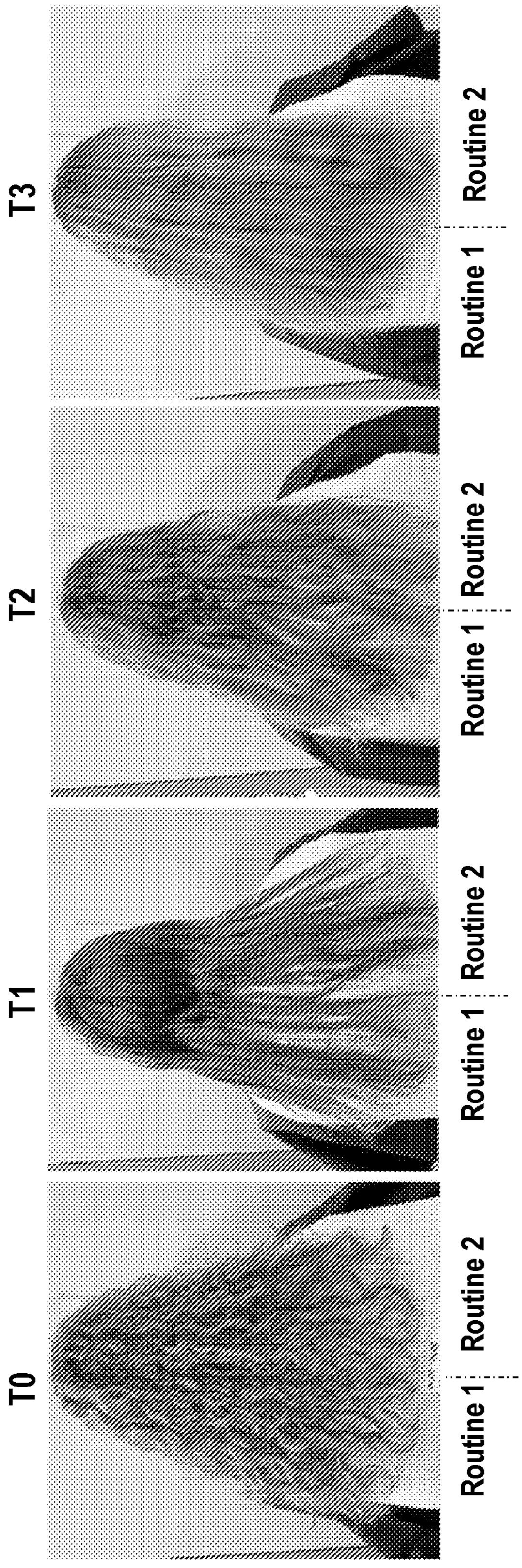

FIGS. 5A-5C are photographic images illustrating the appearance of the hair of three consumers before, during, and after the treatment using composition 1A via two different application routines as described above. The hair on the right side each head was treated with composition 1A via application routine 1, and the hair on the left side of each head was treated with composition 1A via according to routine 2. As can be seen, these consumers had curly hair varied in curly degree and, hair density, length, diameter, and sensitivity. T0 corresponds to the time point before applying composition 1A to the hair; T1 corresponds to the time point right after the application of composition 1A while the hair was still wet; T2 corresponds to the time point six (6) hours after the application of composition 1A and before breaking the film; and T3 corresponds to the time point after breaking the film.

As shown in FIGS. 5A-5C, without heating, the hair treated with composition 1A was significantly straightened and exhibited significant curl reduction, no matter how composition 1A was applied to the hair, either via the standard routine or the new routine. In addition, the hair treated with composition 1A also demonstrated additional noticeable properties such as frizz control, detangling, hair smoothness, no matter how composition 1A was applied. As such, composition 1A can be easily used by a consumer, as via exemplified routine 2.

The above examples demonstrate that compositions according to the disclosure provide effective temporary straightening benefits to curly hair, while at the same time providing one or more additional sensorial benefits such as smoothness and frizz-control to the hair. The straightening effect provided by the compositions according to the present disclosure does not need the use of heat. These various benefits provided by the compositions disclosed herein are lasting, even after the hair is exposed to high humidity condition such as 80% RH for one hour. Furthermore, compositions according to the disclosure are stable either at room temperature or at an elevated temperature such as 45° C. over a period of time of at least two months.

It will be apparent to those skilled in the art that various modifications and variations can be made in the compositions and methods according to the disclosure without departing from the spirit or scope of the disclosure. Thus, it is intended that the disclosure cover such modifications and variations and their equivalents.

The invention claimed is:

1. A hair styling composition for straightening hair, comprising:
   (a) from about 0.5% to about 8% of at least one polyphenol;
   (b) from about 0.1% to about 2% of at least one polysaccharide gum;
   (c) from about 0.1% to about 5% of at least one polymeric emulsifier;
   (d) from about 0.01% to about 1% of glyceryl polyacrylate; and
   (e) water;
   wherein the hair styling composition has a pH of less than 7;
   wherein the hair styling composition is free of sulfide and thiol reducing agents;
   wherein the total combined amount of components (a), (b), (c), and (d) in the hair styling composition is sufficient to straighten hair without the use of sulfide and thiol reducing agents; and
   wherein all amounts are by weight, relative to the total weight of the hair styling composition.

2. The hair styling composition of claim 1, wherein the at least one polyphenol is present in an amount ranging from about 0.5% to about 4% by weight, relative to the total weight of the composition.

3. The hair styling composition of claim 1, wherein the at least one polyphenol comprises tannic acid.

4. The hair styling composition of claim 1, wherein the at least one polysaccharide gum is present in an amount ranging from about 0.1% to about 1% by weight, relative to the total weight of the composition.

5. The hair styling composition of claim 1, wherein the at least one polysaccharide gum is chosen from *sclerotium* gum, gum arabic, tragacanth gum, karaya gum, guar gum, gellan gum, tara gum, locust bean gum, tamarind gum, xanthan gum, dehydroxanthan gum, carrageenan gum, Seneca gum, gellan gum, or mixtures thereof.

6. The hair styling composition of claim 1, wherein the at least one polymeric emulsifier comprises polyacrylamide.

7. The hair styling composition of claim 1, wherein the at least one polymeric emulsifier is present in an amount ranging from about 0.5% to about 4% by weight, relative to the total weight of the composition.

8. The hair styling composition of claim 1, wherein the total amount of glyceryl polyacrylate ranges from about 0.1% to about 0.4% by weight, relative to the total weight of the composition.

9. The hair styling composition of claim 1, further comprising at least one latex type film former chosen from acrylate-based polymers, polyurethane-based polymers, derivatives thereof, or combinations thereof; and wherein the total amount of the latex type film former(s) is up to about 10% by weight, relative to the total weight of the composition.

10. The hair styling composition of claim 9, wherein the acrylate-based polymers or derivatives thereof are chosen from acrylates copolymer of two or more monomers of (meth) acrylic acid or one of their simple ester, styrene/acrylates copolymer, acrylates/ethylhexyl acrylate copolymer, or mixtures thereof.

11. The hair styling composition of claim 1, wherein the total amount of water is at least about 70% by weight, relative to the total weight of the composition.

12. The hair styling composition of claim 1, further comprising from about 1% to about 20% of at least one vegetable oil.

13. The hair styling composition of claim 12, wherein the at least one vegetable oil is chosen from coconut oil, olive oil, castor seed oil, butyrospermum Parkii (Shea) butter, soybean oil, canola oil, rapeseed oil, corn oil, cottonseed oil, palm oil, peanut oil, safflower oil, sesame oil, sunflower oil, linseed oil, palm kernel oil, tung oil, jatropha oil, mustard oil, camelina oil, pennycress oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, walnut oil, or mixtures thereof.

14. The hair styling composition of claim 1, further comprising at least one humectant chosen from sorbitol, sorbitol glycerin, glycerin, propylene glycol, butylene glycol, pentylene glycol, hexylene glycol, dipropylene glycol, diethylene glycol, diglycerol, hyaluronic acid, xylitol, inulin, or mixtures thereof; wherein the at least one humectant is present in an amount ranging from about 0.1% to about 10% by weight, relative to the total weight of the composition.

15. The hair styling composition of claim 1, further comprising at least one ester other than glyceryl polyacrylate, present in an amount ranging from about 0.1% to about 5% by weight, relative to the total weight of the composition.

16. The hair styling composition of claim 1, wherein the composition is free or substantially free of fatty alcohols.

17. A hair styling composition for straightening hair, comprising:
   (a) tannic acid, present in a total amount ranging from about 0.1% to about 2% by weight;
   (b) at least one polysaccharide gum, present in a total amount ranging from about 0.1% to about 2% by weight;
   (c) at least one emulsifier comprising polyacrylamide, present in a total amount ranging from about 0.1% to about 4% by weight;
   (d) glyceryl polyacrylate, present in an amount ranging from about 0.1% to about 0.5% by weight, relative to the total weight of the composition;
   (e) water, present in an amount of at least 70%;
   (f) optionally, at least one latex type film former chosen from acrylate-based polymers, polyurethane-based polymers, derivatives thereof, or combinations thereof, wherein the total amount of latex type film former(s) ranges from about 0.5% to about 3% by weight;
   (g) optionally, at least one vegetable oil;
   (h) optionally, at least one humectant; and
   (i) optionally, at least one ester other than glyceryl polyacrylate;
   wherein:
   all amounts are based on the total amount of the hair styling composition;
   the hair styling composition has a pH of less than 7;
   the hair styling composition is free of sulfide and thiol reducing agents;
   the hair styling composition comprises less than 0.5% of fatty alcohols; and
   the total combined amount of components (a), (b), (c), and (d) in the hair styling composition is sufficient to straighten hair without the use of sulfide and thiol reducing agents.

18. A method for temporarily straightening curly or wavy hair, comprising:
   (i) applying to the hair a hair styling composition comprising:

(a) from about 0.5% to about 8% of at least one polyphenol;
(b) from about 0.1% to about 2% of at least one polysaccharide gum;
(c) from about 0.1% to about 5% of at least one emulsifier comprising polyacrylamide;
(d) from about 0.01% to about 1% of glyceryl polyacrylate;
(e) water;
(f) optionally, at least one latex type film former chosen from acrylate-based polymers, polyurethane-based polymers, derivatives thereof, or combinations thereof;
(g) optionally, at least one vegetable oil;
(h) optionally, at least one humectant; and
(i) optionally, at least one ester other than glyceryl polyacrylate;

wherein the hair styling composition has a pH of less than 7; and wherein the hair styling composition is free of sulfide and thiol reducing agents; and (ii) straightening the hair applied with the hair styling composition by combing through with fingers or a combing tool after the hair is dried, without the use of sulfide and thiol reducing agents.

19. The method of claim 18, wherein the composition is left on the hair before or after coming through the hair until the hair is washed.

20. A hair styling composition for straightening hair, comprising:

(a) from about 0.1% to about 2% of tannic acid;
(b) from about 0.1% to about 1% of at least one polysaccharide gum;
(c) from about 0.1% to about 1.2% of at least one emulsifier comprising polyacrylamide;
(d) from about 0.1% to about 0.5% of glyceryl polyacrylate;
(e) water; and
(f) from about 0.5% to about 3% of at least one latex type film former chosen from acrylate-based polymers, polyurethane-based polymers, derivatives thereof, or combinations thereof wherein the hair styling composition comprises less than 0.5% of fatty alcohols;

wherein the hair styling composition has a pH of less than 7;

wherein the hair styling composition is free of sulfide and thiol reducing agents;

wherein the total combined amount of components (a), (b), (c), and (d) in the hair styling composition is sufficient to straighten hair without the use of sulfide and thiol reducing agents; and wherein all amounts are by weight, relative to the total weight of the hair styling composition.

* * * * *